(12) United States Patent
Kimura

(10) Patent No.: US 11,623,033 B2
(45) Date of Patent: *Apr. 11, 2023

(54) BLOOD COMPONENT SEPARATION DEVICE

(71) Applicant: TERUMO KABUSHIKI KAISHA, Tokyo (JP)

(72) Inventor: Shigeyuki Kimura, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 531 days.

This patent is subject to a terminal disclaimer.

(21) Appl. No.: 16/680,819

(22) Filed: Nov. 12, 2019

(65) Prior Publication Data

US 2020/0078501 A1 Mar. 12, 2020

Related U.S. Application Data

(62) Division of application No. 15/510,592, filed as application No. PCT/JP2015/074099 on Aug. 26, 2015, now Pat. No. 10,518,007.

(30) Foreign Application Priority Data

Sep. 19, 2014 (JP) ................ 2014-191403

(51) Int. Cl.
| | |
|---|---|
| *A61M 1/36* | (2006.01) |
| *A61M 1/02* | (2006.01) |
| *A61M 1/38* | (2006.01) |
| *C12N 5/078* | (2010.01) |
| *B04B 5/04* | (2006.01) |
| *B04B 11/02* | (2006.01) |

(52) U.S. Cl.
CPC ........ *A61M 1/3693* (2013.01); *A61M 1/0209* (2013.01); *A61M 1/0236* (2014.02); *A61M 1/0245* (2013.01); *A61M 1/0272* (2013.01); *A61M 1/385* (2013.01); *B04B 5/0442* (2013.01); *B04B 11/02* (2013.01); *C12N 5/0634* (2013.01); *C12N 5/0644* (2013.01); *A61M 1/3643* (2013.01); *A61M 2202/0427* (2013.01); *A61M 2205/3337* (2013.01); *A61M 2230/207* (2013.01)

(58) Field of Classification Search
CPC . A61M 1/3693; A61M 1/0209; A61M 1/0272
See application file for complete search history.

(56) References Cited

U.S. PATENT DOCUMENTS

| | | | |
|---|---|---|---|
| 5,496,265 | A | 3/1996 | Langley et al. |
| 2003/0066807 | A1 | 4/2003 | Suzuki |
| 2009/0217202 | A1 | 8/2009 | Foley |

FOREIGN PATENT DOCUMENTS

| | | |
|---|---|---|
| EP | 654277 A1 | 5/1995 |
| JP | 07178162 A | 7/1995 |
| JP | 2003088580 A | 3/2003 |
| JP | 2003088581 A | 3/2003 |
| JP | 2005500087 A | 1/2005 |
| JP | 2005110748 A | 4/2005 |
| WO | 2002069793 A2 | 9/2002 |

OTHER PUBLICATIONS

English Translation of the International Search Report for Application No. PCT/JP2015/074099, conducted by the Japanese Patent Office, dated Nov. 24, 2015, 2 pages.

*Primary Examiner* — Michelle F. Paguio Prising
(74) *Attorney, Agent, or Firm* — Sheridan Ross P.C.

(57) ABSTRACT

A blood component separation device for separating a plurality of blood components from blood sampled from a blood donor, and collecting platelets, includes: an operation unit that calculates a predicted platelet recovery rate from a hematocrit value of the blood and a platelet concentration of the blood, and calculates a recommended processing amount of the blood recommended for collecting a target number of units of platelets on the basis of the calculated predicted platelet recovery rate, wherein the operation unit sets the predicted platelet recovery rate calculated from any the hematocrit value and any the platelet concentration to be smaller by a predetermined value a when the blood donor is female than that when the blood donor is male.

13 Claims, 23 Drawing Sheets

FIG. 21

|  | MALE | FEMALE | DIFFERENCE BETWEEN SEXES (PREDETERMINED VALUE $\alpha$) |
|---|---|---|---|
| 2-CYCLE DONOR | 81% | 79% | 2% |
| 3-CYCLE DONOR | 78% | 74% | 4% |
| 4-CYCLE DONOR | 75% | 70% | 5% |

FIG. 22

|  | MALE | FEMALE |
|---|---|---|
| RECOMMENDED CYCLE NUMBER | 3 | 3 |
| PREDICTED PLT NUMBER | 2.04 × 10e11 | 2.04 × 10e11 |
| EXPECTED PREPARATION PLT NUMBER | 2.04 × 10e11 | 1.93 × 10e11 |

FIG. 23

|  | MALE | FEMALE | |
|---|---|---|---|
| RECOMMENDED CYCLE NUMBER | 3 | 3 → | 4 |
| PREDICTED PLT NUMBER | 2.04 × 10e11 | 1.93 × 10e11 | 2.50 × 10e11 |
| EXPECTED PREPARATION PLT NUMBER | 2.04 × 10e11 | 1.93 × 10e11 | 2.50 × 10e11 |

FIG. 24

|  | RANGE OF $\alpha$ |
|---|---|
| 1-CYCLE DONOR | 0 ~ 2.0% |
| 2-CYCLE DONOR | 0 ~ 4.0% |
| 3-CYCLE DONOR | 0 ~ 6.0% |
| 4-CYCLE DONOR | 0 ~ 8.0% |
| 5-CYCLE DONOR | 0 ~ 10.0% |

BLOOD COMPONENT SEPARATION DEVICE

CROSS-REFERENCE TO RELATED APPLICATIONS

This application claims the benefit of Japanese Application No. 2014-191403 filed Sep. 19, 2014 and entitled "Blood Component Separator" and of PCT application No. PCT/JP2015/074099 filed Aug. 26, 2015 and entitled "Blood Component Separation Device", and of U.S. application Ser. No. 15/510592 filed Mar. 10, 2017 entitled "Blood Component Separation Device". The disclosures of the above-identified applications are hereby incorporated by reference in their entireties as if set forth herein in full for all that they teach and for all purposes.

TECHNICAL FIELD

The present invention relates to a blood component separation device for collecting platelets from blood.

BACKGROUND ART

Conventionally, in blood sampling, a blood component sampling in which only platelets and the like are collected and other components are returned to the blood donor (donor) is mainly employed, and at the time of the blood component sampling, a blood component separation device equipped with a centrifugal separator is used.

In recent years, blood transfusion with a platelet liquid is widely conducted in radiation therapy of cancer or the like, and in such a case, a high concentration of platelet liquid is required. For collecting a high-concentration platelet liquid, the technique of Patent Literature 1 collects a target number of units of platelets by conducting a platelet collecting operation for separating blood sampled from a blood donor and collecting platelets in multiple cycles.

CITATION LIST

Patent Literature

Patent Literature 1: JP 2003-88581 A

SUMMARY OF INVENTION

Technical Problem

Here, for collecting a target number of units of platelets, a recommended cycle number of the platelet collecting operation or a recommended processing blood amount (hereinafter, recommended processing amount) is determined on the basis of the predicted platelet recovery rate calculated from the hematocrit value of the blood of the blood donor and the platelet concentration of the blood of the donor. However, the recovery rate of the platelets that is actually collected as a preparation varies depending on the sex of the blood donor according to the difference in circulating blood volume and the difference in blood flow condition between men and women. Therefore, if the predicted platelet recovery rate is determined uniformly regardless of the sex of the blood donor, the aforementioned cycle number of the platelet collecting operation or the recommended processing amount would be insufficient when the donor is female, and inadequacy of units (the target number of units for the collected platelets will not be fulfilled) would occur. Therefore, in order to collect a target number of units of platelets securely, it is sometimes necessary to vary the recommended cycle number of the platelet collecting operation or the recommended processing amount according to the sex of the blood donor. However, Patent Literature 1 does not disclose that the recommended cycle number of the platelet collecting operation or the recommended processing amount is varied according to the sex of the blood donor.

The present invention was devises to solve the aforementioned problems, and it is an object of the present invention to provide a blood component separation device capable of securely collecting a target number of units of platelets regardless of the sex of the blood donor.

Solution to Problem

One aspect of the present invention to solve the problem is a blood component separation device for separating a plurality of blood components from blood sampled from a blood donor, and collecting platelets, including: an operation unit that calculates a predicted platelet recovery rate from a hematocrit value of the blood and a platelet concentration of the blood, and calculates a recommended processing amount of the blood recommended for collecting a target number of units of platelets on the basis of the calculated predicted platelet recovery rate, wherein the operating unit sets the predicted platelet recovery rate calculated from any the hematocrit value and any the platelet concentration to be smaller by a predetermined value $\alpha$ when the blood donor is female than that when the blood donor is male.

According to this aspect, it is possible to calculate the predicted platelet recovery rate correctly according to the sex of the blood donor. Therefore, it is possible to securely collect a target number of units of platelets regardless of the sex of the blood donor.

In this aspect, it is preferable that the predetermined value $\alpha$ increases as the recommended processing amount of the blood increases.

According to this aspect, it is possible to securely collect a target number of units of platelets regardless of the processing amount of blood or the sex of the blood donor.

In this aspect, it is preferable that a) a centrifugal separation step of introducing the blood into a centrifuge, and separating the blood into a plurality of blood components; b) a circulation flow step of introducing plasma among the separated blood components into the centrifuge together with the blood; c) a circulation and acceleration step of introducing only plasma into the centrifuge while stopping feeding of the blood into the centrifuge after the circulation flow step, allowing plasma to further circulate for a predetermined time, and then accelerating a circulation velocity, to separate and collect platelets by the centrifuge, and d) a blood returning step of returning blood components that have not been collected to the blood donor after the circulation and acceleration step, are conducted, the steps a) to d) are conducted as one cycle, and the operation unit calculates a recommended cycle number as the recommended processing amount of the blood.

According to this aspect, it is possible to separate platelets from other blood components with high accuracy. Also, since the collecting timing of a high concentration of platelets is optimized, it is possible to collect many more platelets efficiently. Further, since the recommended cycle number is calculated on the basis of the predicted platelet recovery rate in accordance with the sex of the blood donor, it is possible to securely collect a target number of units of platelets regardless of the sex of the blood donor.

In this aspect, it is preferable that by rotating the separation vessel about an axial center while feeding the blood into the circular separation vessel, the blood in the separation vessel is separated into a plurality of blood components, and platelets are collected from the plurality of separated blood components.

According to this aspect, it is possible to separate platelets from other blood components with high accuracy by a simple device configuration.

Advantageous Effects of Invention

According to the blood component separation device of the present invention, it is possible to securely collect a target number of units of platelets regardless of the sex of the blood donor.

BRIEF DESCRIPTION OF DRAWINGS

FIG. 21 is a chart showing one example of preparation platelet recovery rate according to sex and cycle number.

FIG. 22 is a chart showing recommended cycle number, predicted PLT numbers, and expected preparation PLT numbers in the conventional example.

FIG. 23 is a chart showing recommended cycle numbers, predicted PLT numbers, and expected preparation PLT numbers in the first embodiment.

FIG. 24 is a chart showing examples of the numerical range of predetermined value $\alpha$.

DESCRIPTION OF EMBODIMENTS

Hereinafter, embodiments of the blood component separation device of the present invention will be specifically described on the basis of the attached drawings.

First Embodiment

Figure 1:
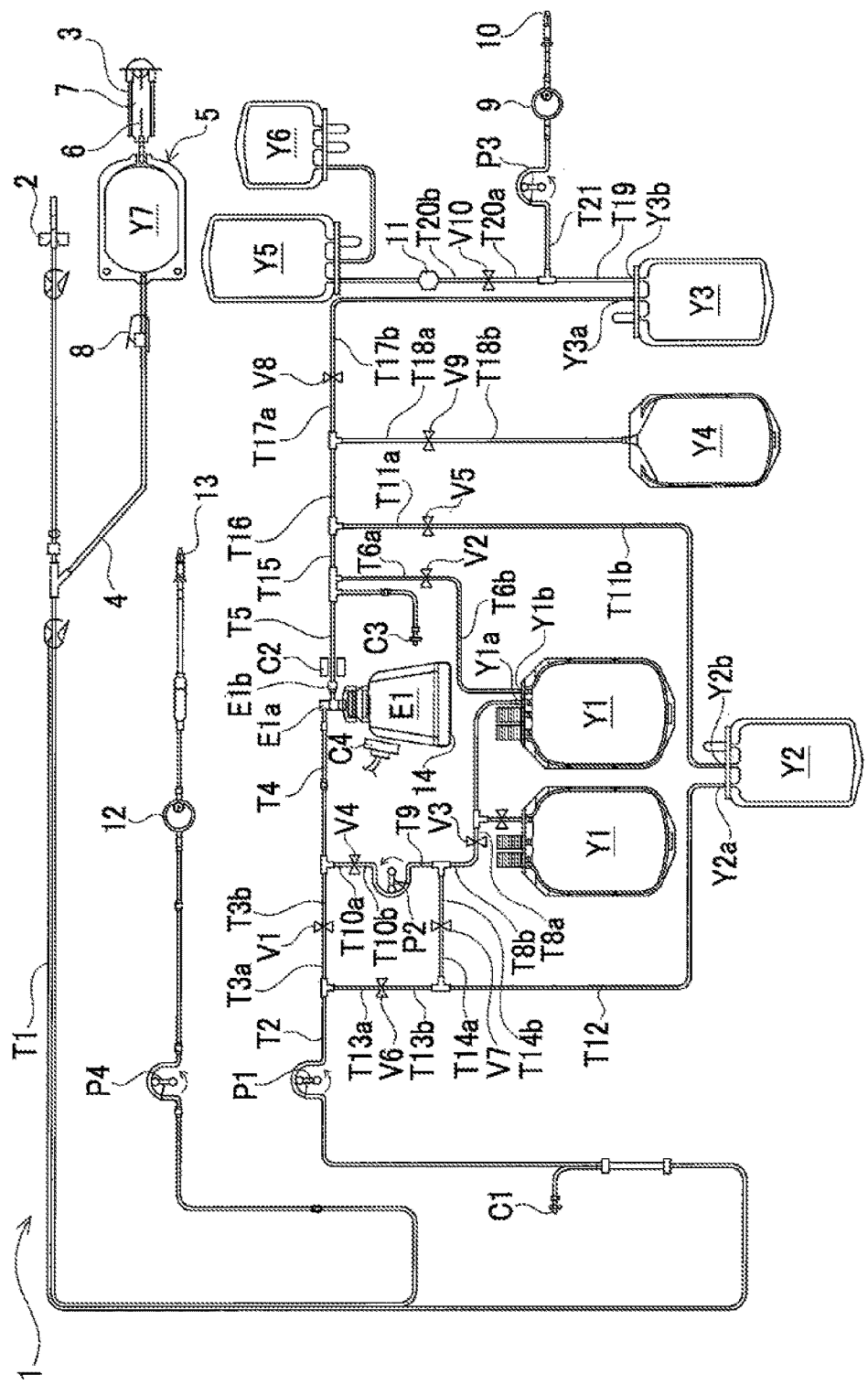
FIG. 1 is a diagram showing a configuration of a blood component separation device in the first embodiment.

As shown in FIG. 1, the blood component separation device of the present embodiment has a blood component separation circuit 1. The blood component separation circuit 1 has a blood sampling needle 2, and an initial flow blood sampling circuit 5 made up of an initial flow blood sampling bag Y7 for sampling initial flow blood, a sampling port 3, and an initial flow blood sampling line 4.

The blood component separation circuit 1 has a centrifugal bowl E1. The centrifugal bowl E1 has a rotor having a blood storage space inside the same (not illustrated), a centrifugal bowl driver 14 which is a rotationally driving means for rotationally driving the rotor, an inflow port (first port) E1a, and an outflow port (second port) E1b, and separate the blood into a plurality of blood components by the rotation of the rotor The blood component separation circuit 1 has a plasma bag (first vessel) Y1, a temporary storage bag (second vessel) Y2, and a platelet intermediate bag (third vessel) Y3 for storing the blood components separated by the centrifugal bowl E1.

The blood component separation circuit 1 has a first line, a second line, a third line, a fourth line, a fifth line, a sixth line, and a seventh line.

The first line is provided for connecting the blood sampling needle 2 and the centrifugal bowl E1, and is made up of a donor tube T1, a first blood pump P1, a tube T2, a tube T3a, a first on-off valve V1, a tube T3b, and a tube T4. The second line is provided for connecting the centrifugal bowl E1 and the plasma bag Y1, and is made up of a tube T5, a tube T6a, a second on-off valve V2, and a tube T6b. The third line is provided for connecting the plasma bag Y1 and the first line, and is made up of a tube T8a, a third on-off valve V3, a tube T8b, a tube T9, a second blood pump P2, a tube T10b, a fourth on-off valve V4, and a tube T10a.

The fourth line is provided for connecting the centrifugal bowl E1 and the temporary storage bag Y2, and is made up of the tube T5, a tube T15, a tube T11a, a fifth on-off valve V5, and a tube T11b. The fifth line is provided for connecting the temporary storage bag Y2 and the first line, and is made up of a tube T12, a tube T13b, a sixth on-off valve V6, and a tube T13a. Likewise the fifth line, the sixth line is provided for connecting the temporary storage bag Y2 and the first line, and is made up of the tube T12, a tube T14a, a seventh on-off valve V7, a tube T14b, the tube T9, the second blood pump P2, the tube T10b, the fourth on-off valve V4, and the tube T10a. The seventh line is provided for connecting the centrifugal bowl E1 and the platelet intermediate bag Y3, and is made up of the tube T5, the tube T15, a tube T16, a tube Tl7a, an eighth on-off valve V8, and a tube Tl7b.

The blood sampling needle 2 which is a sampling means for sampling whole blood (blood) from a blood donor (donor) is connected to the first port of the first blood pump P1 by the donor tube T1. The initial flow blood sampling bag Y7 is connected to the blood sampling needle from a branch part provided on the donor tube T1 by the initial flow blood sampling line 4. The initial flow blood sampling bag Y7 further has the sampling port 3 for transferring the sampled initial flow blood to a test vessel that is not illustrated, and the sampling port 3 is made up of a body part, a needle part 6, and a cover part 7 for covering the needle part. On the initial flow blood sampling line 4, a clamp 8 for opening or closing the line is provided.

The tube T2 connecting to the second port of the first blood pump P1 is branched into two tubes T3a and Tl3a, and the tube T3a is connected to the first port of the first on-off valve V1, and the second port of the first on-off valve V1 is connected to the tube T3b. The tube T3b is branched into two tubes T4 and T10a, and the tube T4 connects to the inflow port E1a of the centrifugal bowl E1 which is a centrifuge for separating the sampled blood into a plurality of blood components. The centrifugal bowl E1 is disposed on the centrifugal bowl driver 14 and rotationally driven.

The blood sampling needle 2, and the inflow port E1a on the inlet side of the centrifugal bowl E1 are connected by the first line (the donor tube T1, the first blood pump P1, the tube T2, the tube T3a, the first on-off valve V1, the tube T3b, and the tube T4).

To the donor tube T1, a pressure sensor C1 is connected.

The tube T5 connecting to the outflow port E1b of the centrifugal bowl E1 is branched into the tube T15, and the tube T6a. The tube T6a connects to the first port of the second on-off valve V2, and the second port of the second on-off valve V2 connects to the tube T6b. The tube T6b connects to a second port Y1b of the plasma bag Y1.

The outflow port E1b of the centrifugal bowl E1 and the plasma bag Y1 are connected by the second line (the tube T5, the tube T6a, the second on-off valve V2, and the tube T6b). Two plasma bags Y1 are provided, and only one of them is illustrated in FIG. 6 to FIG. 18.

A first port Yla which is the output side of the plasma bag Y1 connects to the tube T8a. The tube T8a connects to the first port of the third on-off valve V3. The second port of the third on-off valve V3 connects to the tube T8b, and the tube T8b connects to the tube T9. The tube T9 connects to the second port of the second blood pump P2. The first port of the second blood pump P2 connects to the tube T10b, and the tube Tin connects to the second port of the fourth on-off valve V4. The first port of the fourth on-off valve V4 connects to the tube T10a.

The tube T10a connects to an intermediate position of the tube T3b and the tube T4 forming the first line. That is, the plasma bag Y1 and the first line are connected by the third line (the tube T8a, the third on-off valve V3, the tube T8b, the tube T9, the second blood pump P2, the tube T10b, the fourth on-off valve V4, and the tube T10a). Thus, the plasma bag Y1 is connected so that it selectively communicates with the inlet side or the outlet side of the centrifugal bowl E1.

The tube T15 branched from the tube T5 is further branched into the tube T11a, and the tube T16. The tube Tlla connects to the first port of the fifth on-off valve V5, and the second port of the fifth on-off valve V5 connects to the tube Tllb. The tube Tllb connects to the second port Y2b of the temporary storage bag Y2. That is, the outflow port E1b of the centrifugal bowl E1, and the temporary storage bag Y2 are connected by the fourth line (the tube T5, the tube T15, the tube Tlla, the fifth on-off valve V5, and the tube T11b).

A first port Y2a of the temporary storage bag Y2 connects to the tube T12, and branches into the tube T13b and the tube T14a. The tube T13b connects to the first port of the sixth on-off valve V6, and the second port of the sixth on-off valve V6 connects to the tube T13a. The tube T13a connects to an intermediate position of the tube T2, and the tube T3a forming the first line.

Meanwhile, the tube T14a branched from the tube T12 connects to the first port of the seventh on-off valve V7, and the second port of the seventh on-off valve V7 connects to the tube T14b. The tube T14b connects to an intermediate position of the tube T9, and the tube T8b, and the tube T9 connects to the second port of the second blood pump P2.

The first port of the second blood pump P2 connects to the tube T10b, and the tube T10b connects to the first port of the fourth on-off valve V4. The second port of the fourth on-off valve V4 connects to the tube T10a. The tube T10a connects to an intermediate position of the tube T3b, and the tube T4 forming the first line. That is, the temporary storage bag Y2 and the first line are connected by the fifth line (the tube T12, the tube T13b, the sixth on-off valve V6, and the tube T13a), and the sixth line (the tube T12, the tube T14a, the seventh on-off valve V7, the tube T14b, the tube T9, the second blood pump P2, the tube T10b, the fourth on-off valve V4, and the tube T10a). The temporary storage bag Y2 is connected so that it selectively communicates with the inlet side or the outlet side of the centrifugal bowl E1.

Meanwhile, the tube T16 branched from the tube T15 further branches into two tubes, the tube T17a and a tube T18a. The tube T17a connects to the first port of the eighth on-off valve V8, and the second port of the eighth on-off valve V8 connects to the tube T17b. The tube T17b connects to a first port Y3a which is an input side of the platelet intermediate bag Y3. Meanwhile, the tube T18a branched from the tube T16 connects to the first port of a ninth on-off valve V9, and the second port of the ninth on-off valve V9 connects to a tube T18b. The tube T18b connects to an air bag Y4. That is, the outflow port E1b of the centrifugal bowl E1 and the platelet intermediate bag Y3 are connected by the seventh line (the tube T5, the tube T15, the tube T16, the tube T17a, the eighth on-off valve V8, and the tube T17b). Thus, the platelet intermediate bag Y3 is connected so that it communicates with the outlet side of the centrifugal bowl E1.

To the tube T5 that connects to the outflow port E1b of the centrifugal bowl E1, a turbidity sensor C2 for detecting concentration of the platelets, and a pressure sensor C3 are attached. The turbidity sensor C2 detects the degree of the plasma passing inside the tube T5 to have a turbid condition by platelets.

In the vicinity of the part where the centrifugal bowl E1 is attached, an interface sensor C4 for detecting the interface position of a buffy coat layer BC (see FIG. 3) formed in the centrifugal bowl E1 is attached.

A tube T19 exiting from the second port Y3b which is the output side of the platelet intermediate bag Y3 is branched into two tubes, a tube T20a, and a T21, and the tube T20a connects to the first port of a tenth on-off valve V10, and the second port of the tenth on-off valve V10 connects to a tube T20b. The tube T21 connects to the first port which is the output side of a third blood pump P3. The second port which is the input side of the third blood pump P3 connects to a platelet preservative liquid bottle by a bottle needle 10 through a sterilization filter 9. The tube T20b connects to a platelet bag Y5 through a white blood cell removal filter 11. To the platelet bag Y5, an air bag Y6 is connected.

Meanwhile, in the halfway of the donor tube T1, an output port of an ACD pump P4 is connected. An input port of the ACD pump P4 is connected to an output port of a sterilization filter 12. An input port of the sterilization filter 12 connects to an ACD storage bottle by a bottle needle 13.

Figure 2:
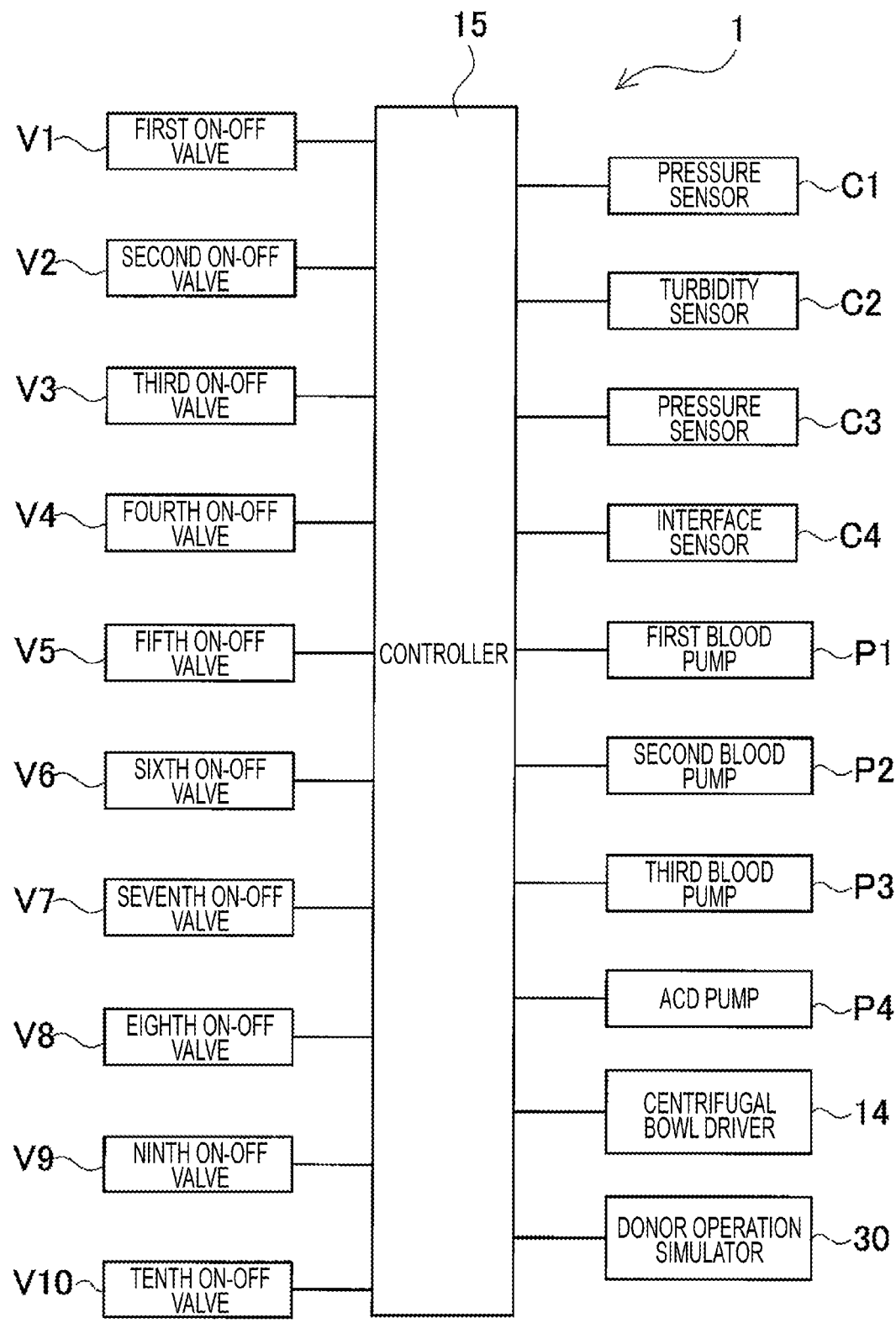
FIG. 2 is a block diagram showing a control system of the blood component separation device in the first embodiment.

As shown in FIG. 2, a controller 15 provided in the blood component separation device of the present embodiment is configured, for example, by a microcomputer, and the first blood pump P1, the second blood pump P2, the third blood pump P3, the ACD pump P4, the centrifugal bowl driver 14, the pressure sensor C1, the turbidity sensor C2, the pressure sensor C3, the interface sensor C4, the first on-off valve V1, the second on-off valve V2, the third on-off valve V3, the fourth on-off valve V4, the fifth on-off valve V5, the sixth on-off valve V6, the seventh on-off valve V7, the eighth on-off valve V8, the ninth on-off valve V9, and the tenth on-off valve V10, and a donor operation simulator 30 are electrically connected to the controller 15.

A detection signal from each of the sensors C1, C2, C3, and C4 is inputted to the controller 15 at any time. The controller 15 controls operation/stopping, the direction of rotation (forward rotation/reverse rotation) and the number of rotation of each of the pumps P1, P2, P3, and P4 on the basis of these detection signals or the like, and controls opening/closing of each the on-off valves V1, V2, V3, V4, V5, V6, V7, V8, V9, and V10 and actuation of the centrifugal bowl driver 14 as needed.

The controller 15 inputs/outputs information with the donor operation simulator 30. The donor operation simulator 30 calculates a predicted platelet recovery rate (a rate of the predicted number of collected platelets to the number of platelets in the blood being processed) from a hematocrit value of blood sampled from a blood donor, and a platelet concentration in blood sampled from the blood donor. Then the donor operation simulator 30 calculates a recommended cycle number or a recommended processing amount of the platelet collecting operation (a series of processes of separating blood sampled from a blood donor and collecting platelets) on the basis of the predicted platelet recovery rate calculated in the manner as described above. The donor operation simulator 30 is one example of "operation unit" of the present invention.

Examples of the material forming a tube include polyvinyl chloride, polyethylene, polypropylene, polyester such as PET or PBT, and various thermoplastic elastomers such as ethylene-vinyl acetate copolymer (EVA), polyurethane, and polyester elastomer, and among these, polyvinyl chloride is particularly preferred. Polyvinyl chloride gives sufficient flexibility and softness, and is easy to handle, and also suited for choking by a clamp or the like.

As the material forming a bag, soft polyvinyl chloride in which DEHP is used as a plasticizer, polyolefins, polymers obtained by polymerizing or copolymerizing olefin or diolefin such as ethylene, propylene, butadiene, and isoprene can be used, and ethylene-vinyl acetate copolymer (EVA) and any combinations of these such as polymer blends of EVA and various thermoplastic elastomers can be recited. Further, it is also possible to use PET, PBT, PCGT and so on. Among these, polyvinyl chloride is particularly preferred, however, for a vessel for storing platelet PLT, those having excellent gas permeability are preferred to improve the storage stability of platelet PLT, and it is preferred to use polyolefin or DnDP-plasticized polyvinyl chloride, or those having a reduced thickness of the sheet.

Figure 3:
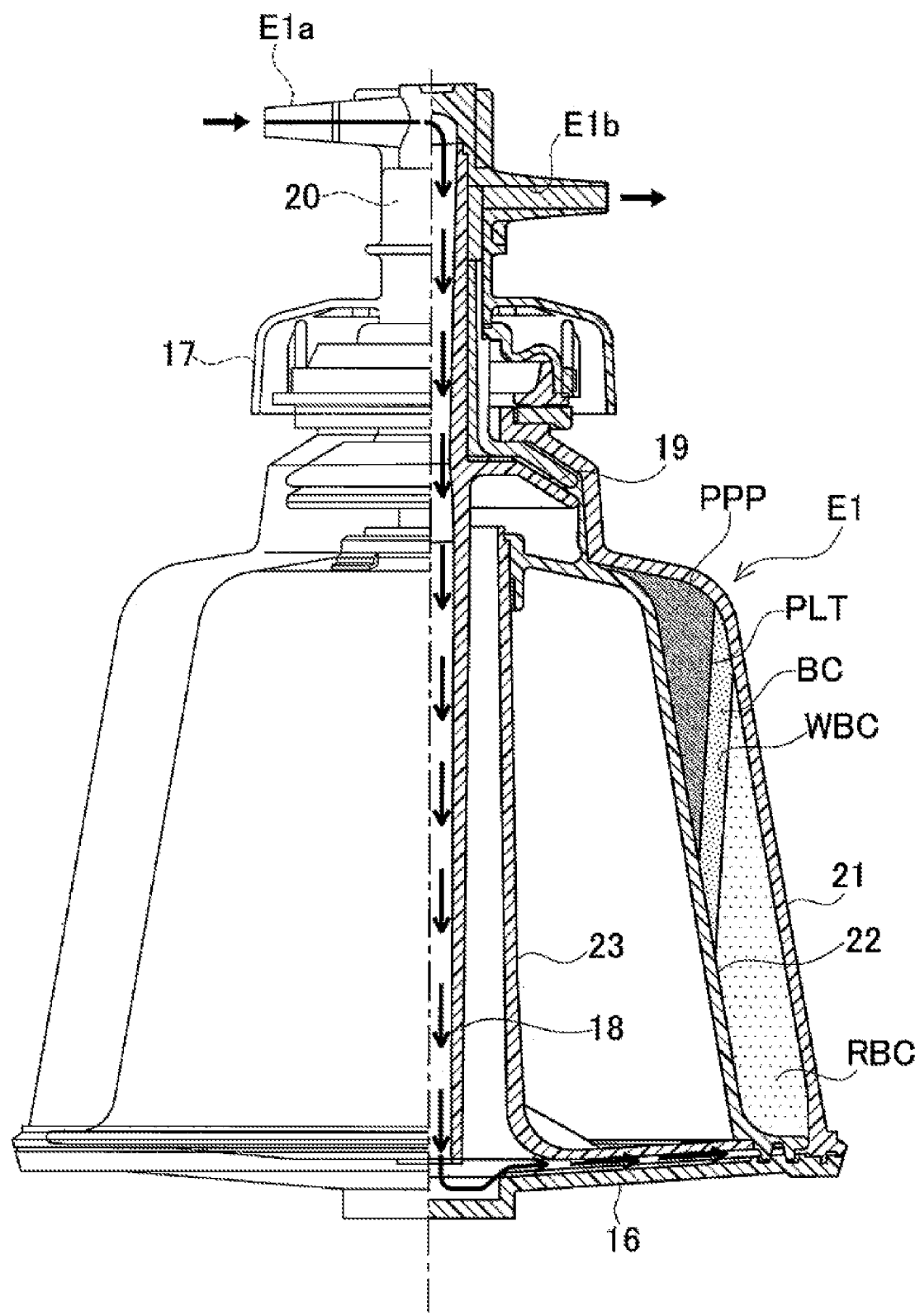
FIG. 3 is a view showing a structure of a centrifugal bowl.

FIG. 3 shows a structure of the centrifugal bowl E1. The right side of the center line is a section view, and the left side is an outside drawing.

A stationary part 20 which is a non-rotating stationary part is formed with the inflow port E1a, and the outflow port E1b. To the stationary part 20, a cover 17, and an inflow channel 18 extending downward are connected. For these stationary parts, a lateral wall 21, an outer shell 22, an inner shell 23, and a bottom plate 16 are integrally held in a rotatable manner. The bottom plate 16 is, for example, adsorbed to the centrifugal bowl driver 14 (see FIG. 1), and rotatory force is given to the bottom plate 16 by the centrifugal bowl driver 14. FIG. 3 shows the state that whole blood is fed into the centrifugal bowl E1 from the inflow port E1a, and blood components are separated by centrifugal force.

In the space formed by the outer shell 22 and the lateral wall 21, a red blood cell layer (RBC layer), a white blood cell layer (WBC layer), a buffy coat layer (BC layer), a platelet layer (PLT layer), and a plasma layer (PPP layer) are formed in the descending order of the magnitude of the specific gravity from outside by the centrifugal force. Here, the white blood cell layer and the platelet layer are difficult to separate from each other because they are close to each other in specific gravity. Therefore, there is the buffy coat layer containing both the white blood cell layer and the platelet layer. In general, whole blood is composed of approximately 55% of plasma PPP, approximately 43.2% of red blood cell RBC, approximately 1.35% of white blood cell WBC, and approximately 0.45% of platelet PLT.

In the centrifugal bowl E1, since an outflow channel 19 that is formed slightly upstream the intermediate point of the inflow channel 18 is formed in the inner circumferential part, the plasma layer (PPP layer) formed in the inner circumference in the space formed by the outer shell 22 and the lateral wall 21 first flows out of the centrifugal bowl E1 through the outflow port E1b.

Next, an operation of the blood component separation device having the above configuration will be described.

Before starting blood sampling, a recommended cycle number of the platelet collecting operation is determined by the donor operation simulator 30. In the present embodiment, the donor operation simulator 30 calculates a predicted platelet recovery rate according to the sex from a blood count value of blood that is preliminarily sampled from a blood donor, and on the basis of the predicted platelet recovery rate thus calculated, a recommended cycle number of the platelet collecting operation is calculated. Then the blood component separation device starts blood sampling in the following manner. The details of the method of calculating the recommended cycle number of the platelet collecting operation by the donor operation simulator 30 will be described later.

Figure 6:
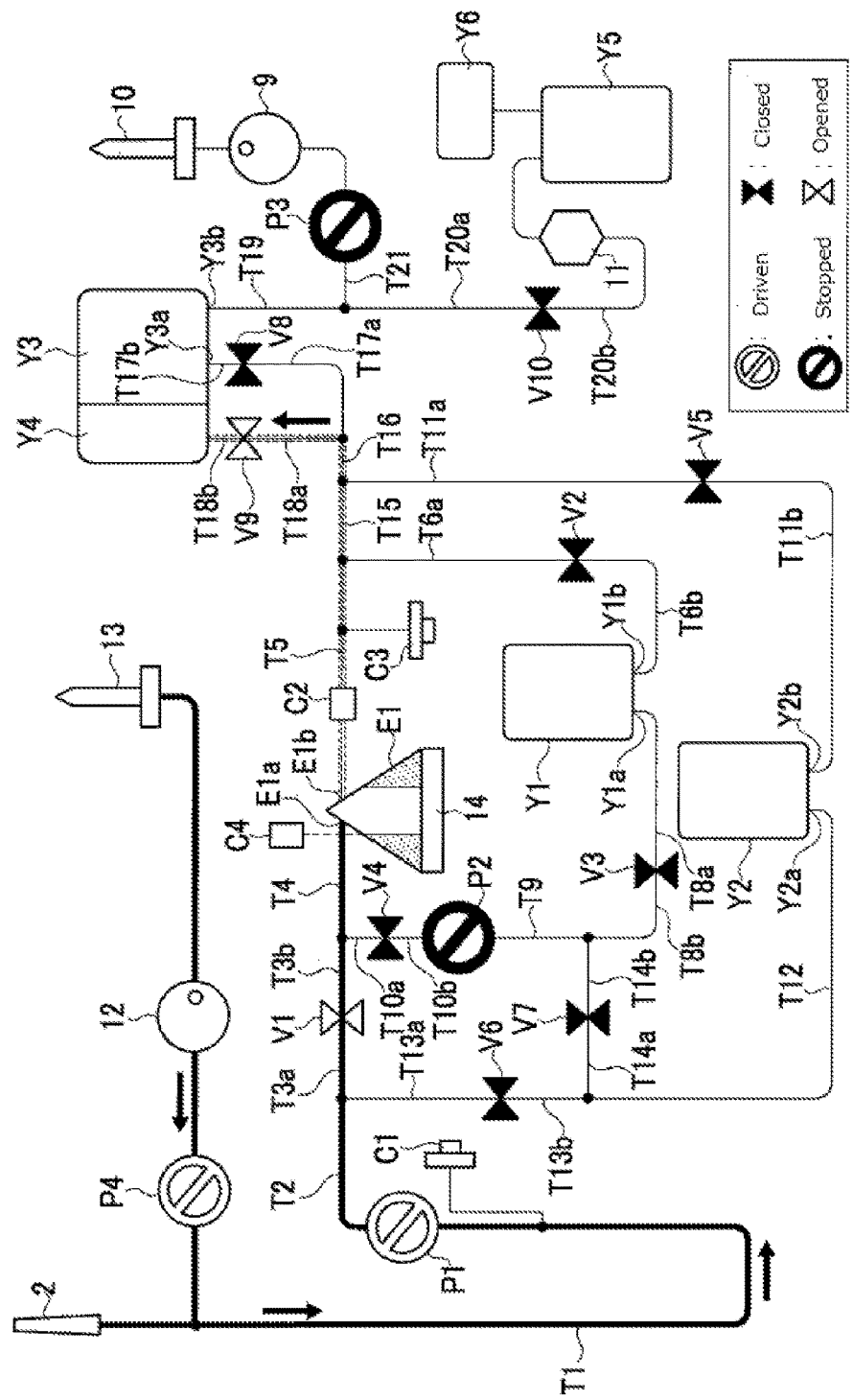
FIG. 6 is a diagram showing a first step (blood sampling starting step).

FIG. 6 is a diagram showing a blood sampling starting step (first step). Among the pumps, the pump indicated by an outline mark is in an operating state, and the pump indicated by a solid mark is in a stopping state. Among the on-off valves, the valve indicated by an outline mark is in an open state, and the valve indicated by a solid mark is in a closed state.

Figure 4:
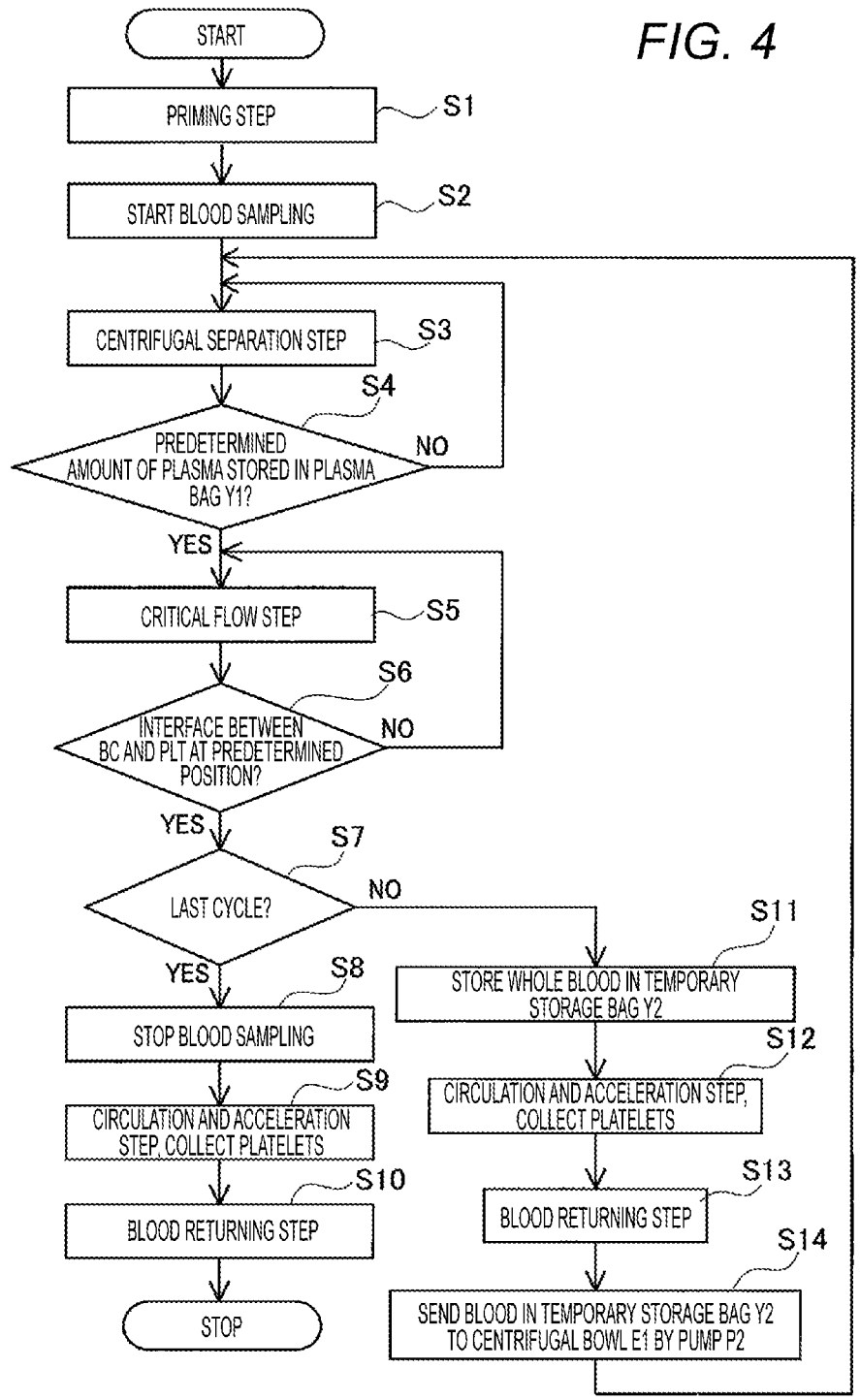
FIG. 4 is a flowchart showing an operation of the blood component separation device in the first embodiment.

First, a priming step (S1) in FIG. 4 is conducted. The ACD pump P4, and the first blood pump P1 are driven, and an ACD liquid for preventing coagulation of blood is fed to the centrifugal bowl E1 via the open first on-off valve V1 to conduct a priming step (S1) of the centrifugal bowl E1, the first blood pump P1 and so on. The priming is a step of preliminarily adhering the ACD liquid to the part with which blood is to come into contact, such as inside the donor tube T1, the first blood pump P1, and the centrifugal bowl E1 so that the blood will not coagulate when it is flown therein.

From the priming step, the centrifugal bowl E1 rotates at a predetermined number of rotation by the centrifugal bowl driver 14.

Upon end of the priming step (S1), a blood donor is punctured with the blood sampling needle 2, and sampling of whole blood is started (S2). After puncturing a blood donor with the blood sampling needle 2, initial flow blood is collected in the initial flow blood sampling bag Y7 (see FIG. 1) in the initial flow blood sampling circuit. It is so configured that in the branch part provided on the donor tube T1, the blood sampling needle 2 and the initial flow blood sampling line 4 (see FIG. 1) are initially connected with each other. After a predetermined amount of blood has stored in the initial flow blood bag, the initial flow blood sampling line 4 is clamped by the clamp 8 (see FIG. 1) to secure a flow channel on the side of the first blood pump P1 of the donor tube T1.

Also at this time, the ACD pump P4 is driven, and the ACD liquid is fed to the donor tube T1, and mixed with the whole blood, and the whole blood is fed to the centrifugal bowl E1. When the whole blood is fed to the rotating centrifugal bowl E1, the air in the centrifugal bowl E1 (indicated by the dotted line) flows out as shown in FIG. 6 from the outflow channel 19 situated in an inner circumferential part of the centrifugal bowl E1 (see FIG. 3) while it is pushed by plasma PPP. The flowing out air is stored in the air bag Y4 via the ninth on-off valve V9 in an open state.

In the centrifugal bowl E1, by giving the centrifugal force to the fed whole blood in the bowl as shown in FIG. 3, the whole blood is separated into different components.

Figure 7:
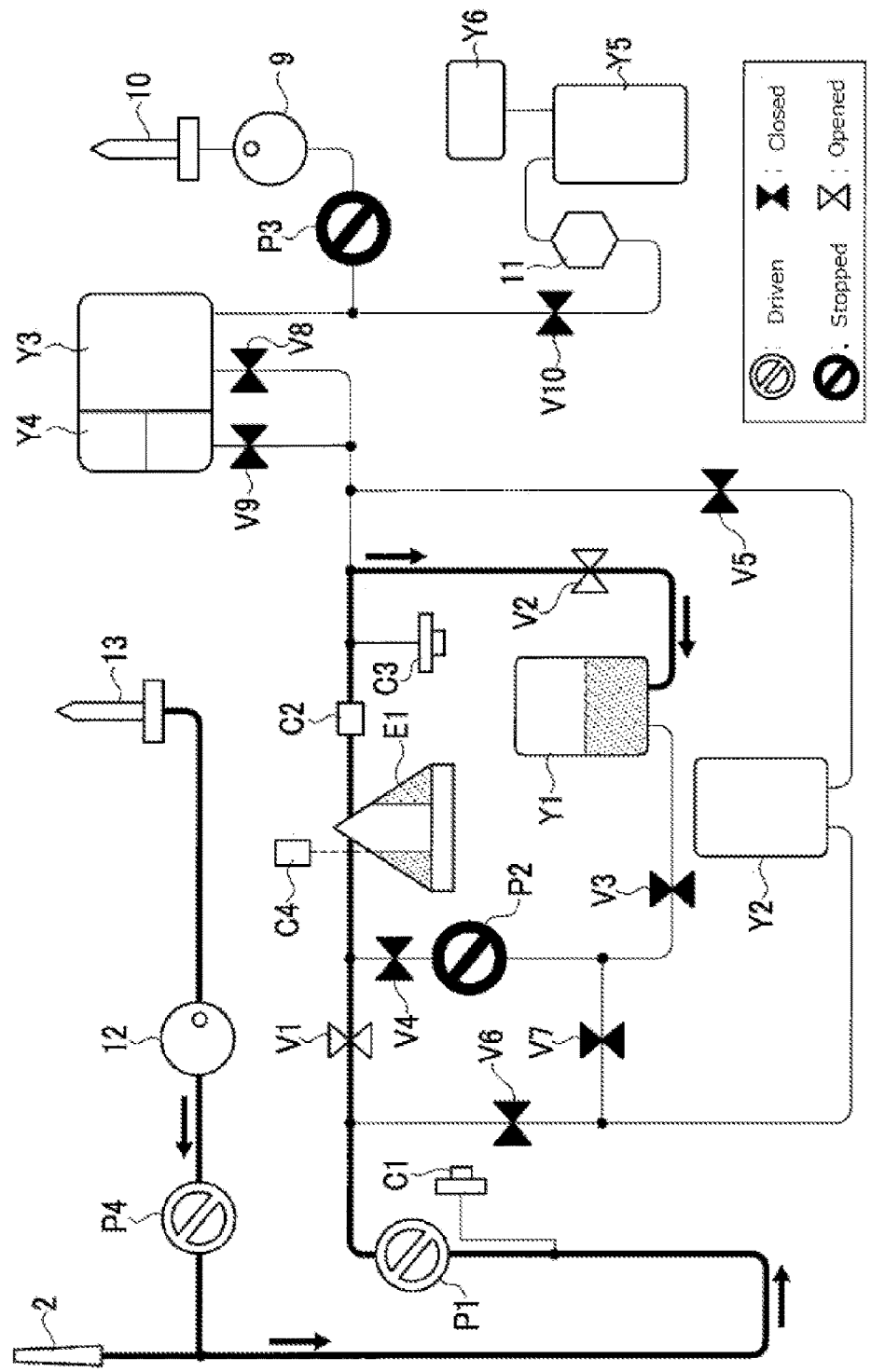
FIG. 7 is a diagram showing a second step (centrifugal separation step).

Then when the turbidity sensor C2 detects that the fluid flowing in the tube changes from the air to plasma PPP, the ninth on-off valve V9 is closed, and the second on-off valve V2 is opened as shown in FIG. 7 to store plasma PPP overflowing from the centrifugal bowl E1 in the plasma bag Y1. This is a centrifugal separation step (S3). As shown in FIG. 3, initially only plasma PPP flows out from the centrifugal bowl E1.

Figure 8:
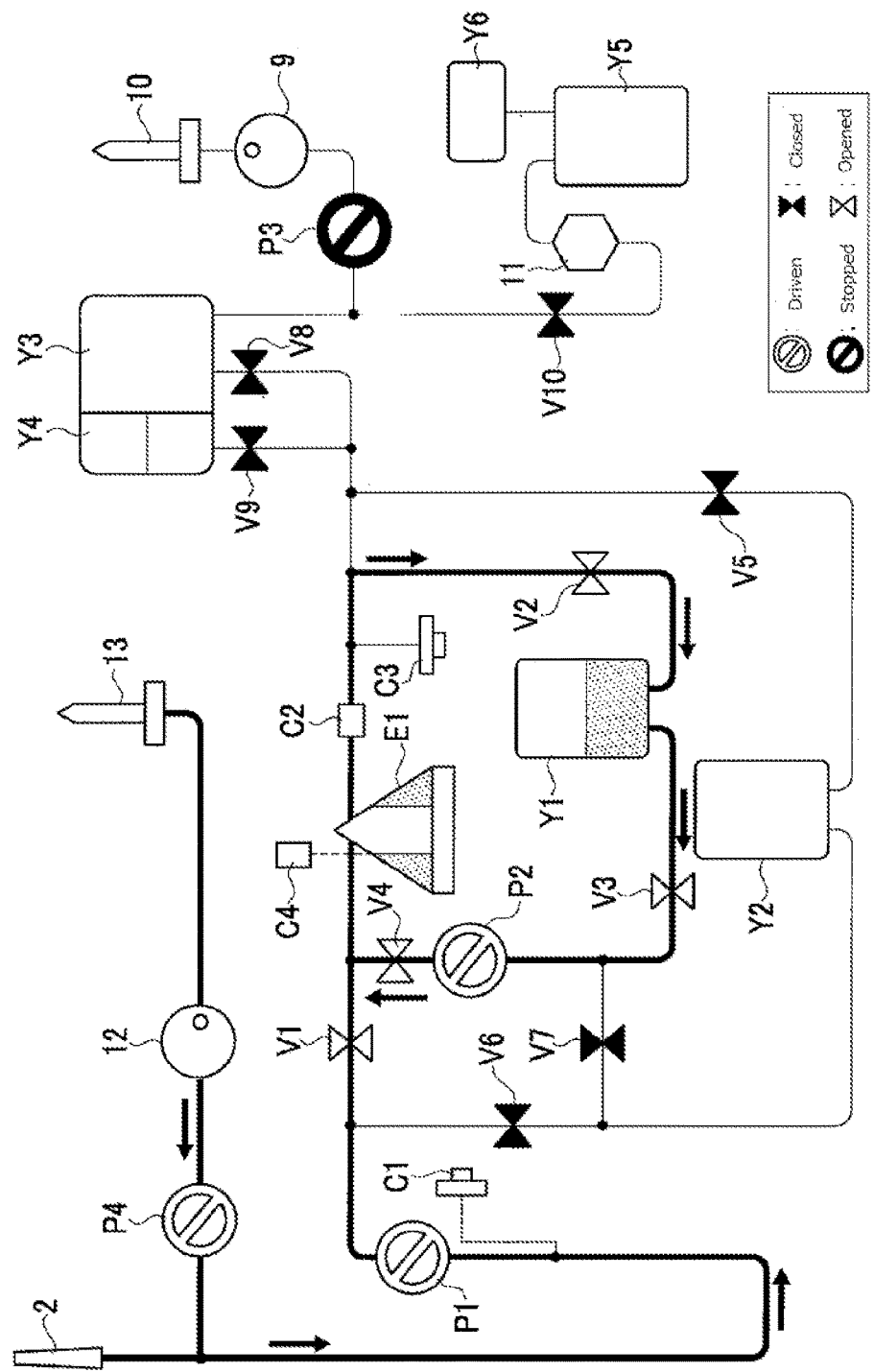
FIG. 8 is a diagram showing a third step (critical flow step).
Figure 19:
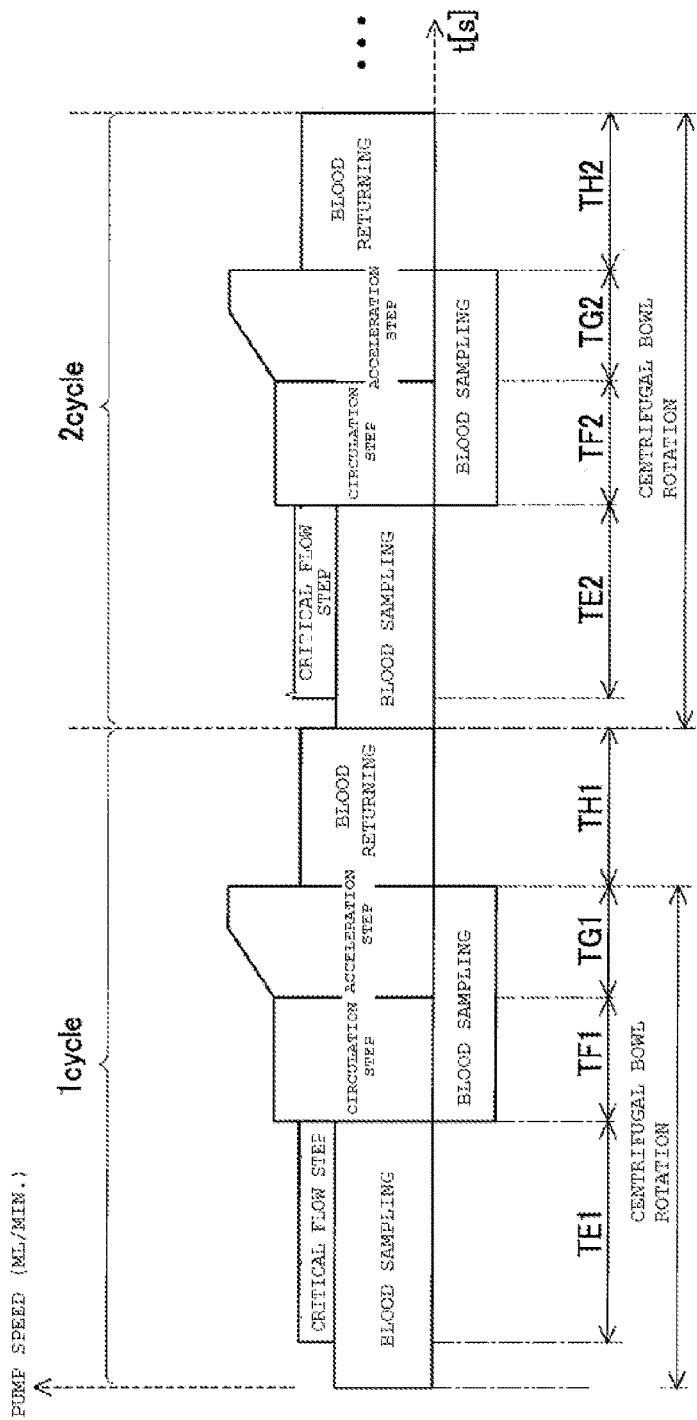
FIG. 19 is a diagram showing the operation of the blood component separation device with time.

Then when a predetermined amount of plasma PPP (30 mL in the present embodiment) has been stored in the plasma bag Y1 (S4: YES), the third on-off valve V3 is opened and the second blood pump P2 is driven as shown in FIG. 8, and further the fourth on-off valve V4 is opened, and whole blood is sampled from the blood donor, and plasma PPP stored in the plasma bag Y1 is mixed with the whole blood, and fed to the centrifugal bowl E1. This is a third step (critical flow step) (S5). This is a critical flow period TE shown in FIG. 19. The critical flow step is one example of "circulation flow step" of the present invention.

Figure 9:
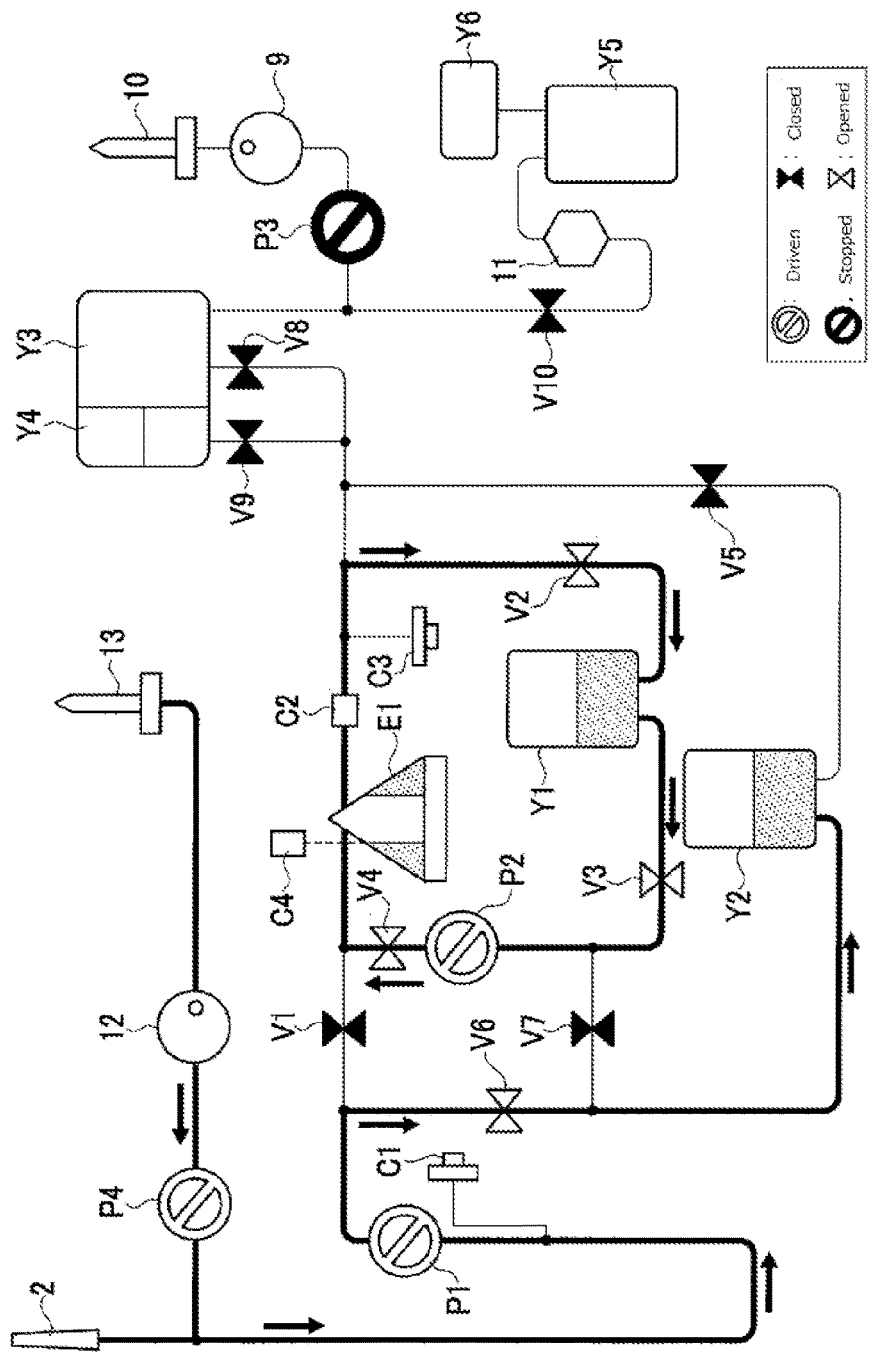
FIG. 9 is a diagram showing a circulation step in the fourth step (circulation and acceleration step).

Then when the interface sensor C4 detects that the interface between the buffy coat layer (BC layer) and the red blood cell layer (RBC layer) in FIG. 3 has reached a predetermined position (S6: YES), the first on-off valve V1 is closed as shown in FIG. 9, and a circulation step (fourth step) of the circulation and acceleration step is conducted for returning plasma PPP in the plasma bag Y1 again into the plasma bag Y1 through the third on-off valve V3, the second blood pump P2, the fourth on-off valve V4, the centrifugal bowl E1, and the second on-off valve V2 while keeping the second on-off valve V2, the third on-off valve V3, and the fourth on-off valve V4 open, and keeping the second blood pump P2 driven. This is a circulation period TF shown in FIG. 19.

Simultaneously, whether the current cycle is the last cycle is determined, and if the current cycle is not the last cycle (S7: NO), the sixth on-off valve V6 is opened, and the first blood pump P1 is kept driven, and the sampled whole blood is stored in the temporary storage bag Y2 (S11). In other words, by storing the sampled whole blood in the temporary storage bag Y2, sampling of whole blood is continued. The sampling of whole blood is continued until the circulation and acceleration step ends, or continued until a predetermined time ora sampling amount is fulfilled. If the current cycle is the last cycle (S7: YES), the first blood pump P1 is stopped and the blood sampling is stopped (S8).

In the circulation step of the circulation and acceleration step in the present embodiment, the circulation velocity is increased compared with that in the critical flow step, and plasma PPP is caused to pass through the centrifugal bowl E1 and circulate for about 30 to 40 seconds at a velocity of about 100 mL/minute. This causes reduction in concentration of a particulate matter in the buffy coat layer BC in FIG. 3, and results in deposition of white blood cell WBC having a larger specific gravity than platelet PLT on the outer side of the buffy coat layer (BC layer). That is, it is possible to separate the platelet layer (PLT layer) from the white blood cell layer (WBC layer) more clearly.

Figure 10:
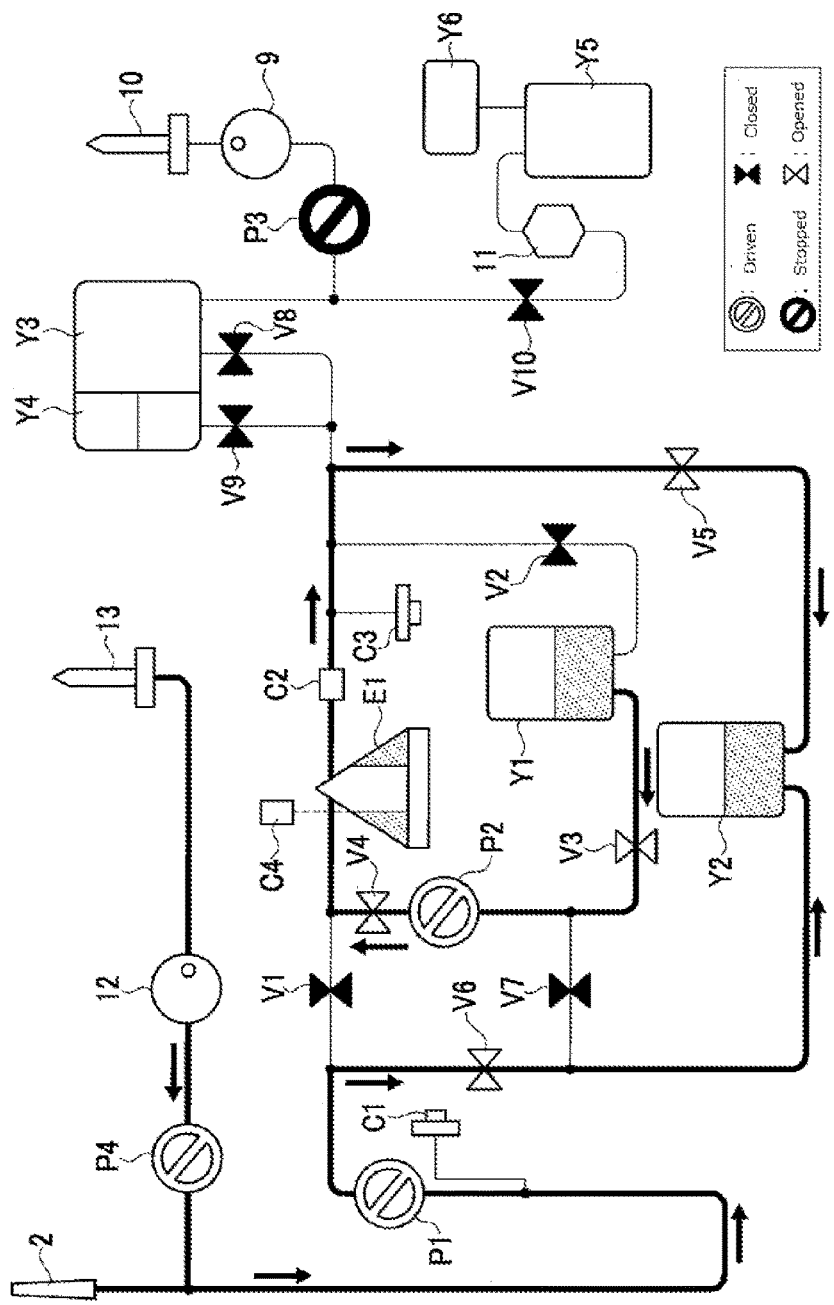
FIG. 10 is a diagram showing a step of recovering a low-concentration platelet liquid in a fifth step (circulation and acceleration step).

Then after conducting the circulation step for a certain time, the process enters the acceleration step (fifth step) of the circulation and acceleration step shown in FIG. 10. In the acceleration step, by controlling the number of rotation of the second blood pump P2, the flow rate of plasma PPP is gradually increased by gradually increasing the number of rotation. In the present embodiment, the flow rate is increased from 100 mL/min., and the flow rate of plasma PPP is accelerated until platelet PLT begins flowing out. This is an acceleration period TG shown in FIG. 19. In FIG. 4, the circulation step and the acceleration step are collectively expressed as the circulation and acceleration step (S9, S12).

By this acceleration step, in FIG. 3, platelet PLT is supplied with the force in the direction of elevation, and is discharged outside the centrifugal bowl E1 from the outflow channel 19. By this acceleration, the white blood cell layer (WBC layer) and the red blood cell layer (RBC layer) having high specific gravity do not exit the outflow channel 19 because the centrifugal force is dominant.

Figure 20:
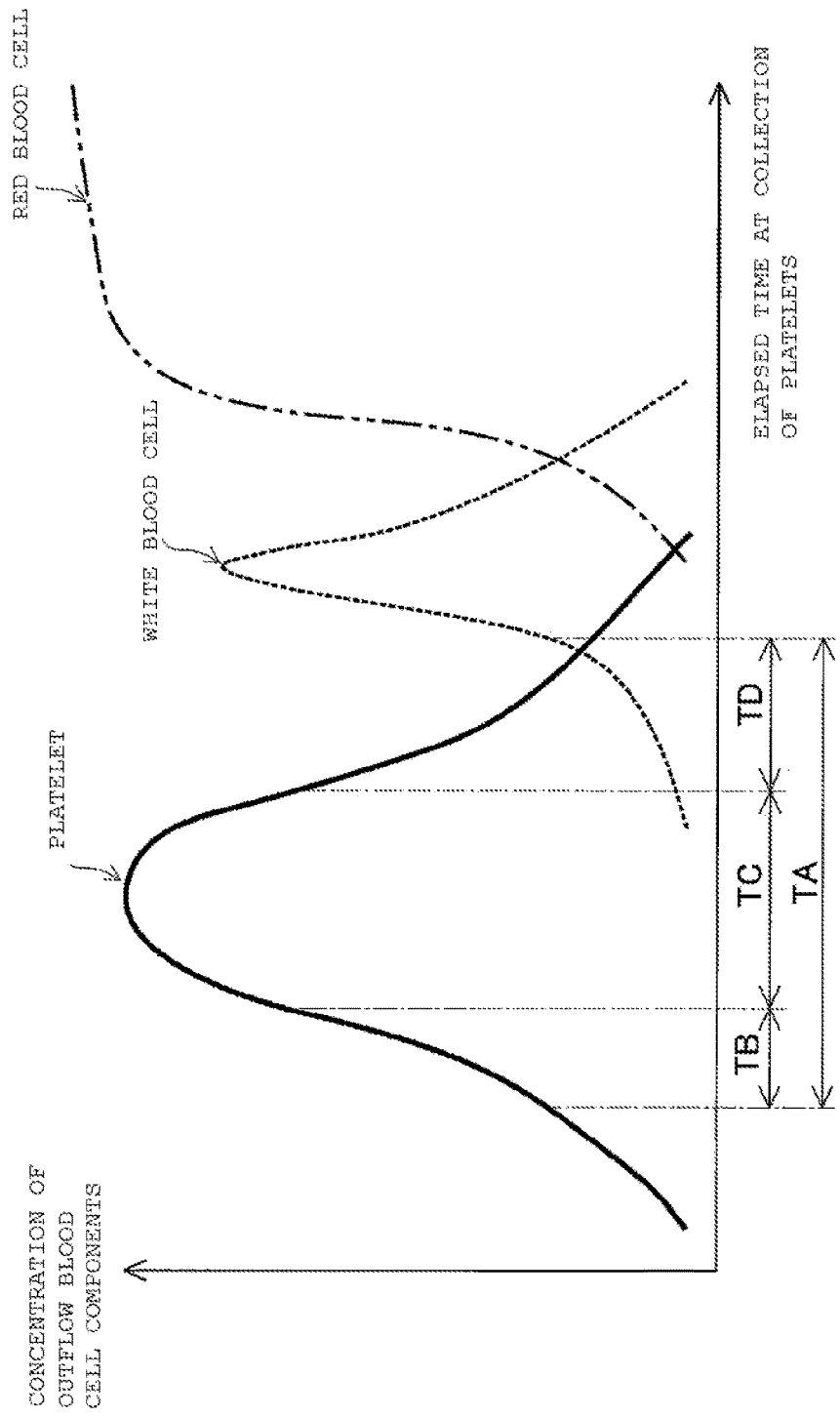
FIG. 20 is a chart showing changes in effluent concentrations of platelet, white blood cell, and red blood cell.

FIG. 20 shows change in concentration of outflow platelet PLT, white blood cell WBC, and red blood cell RBC. The horizontal axis indicates the lapse time in collecting platelet PLT, and the vertical axis indicates concentrations of outflow blood cell components. Initially, platelet PLT flows out (outflowperiodTA), and the amount of outflow platelet PLT gradually increases, and it gradually decreases after passing the maximum flow rate. Likewise in case of white blood cell, the outflow amount gradually increases, and it gradually decreases after passing the maximum flow rate.

Figure 5:
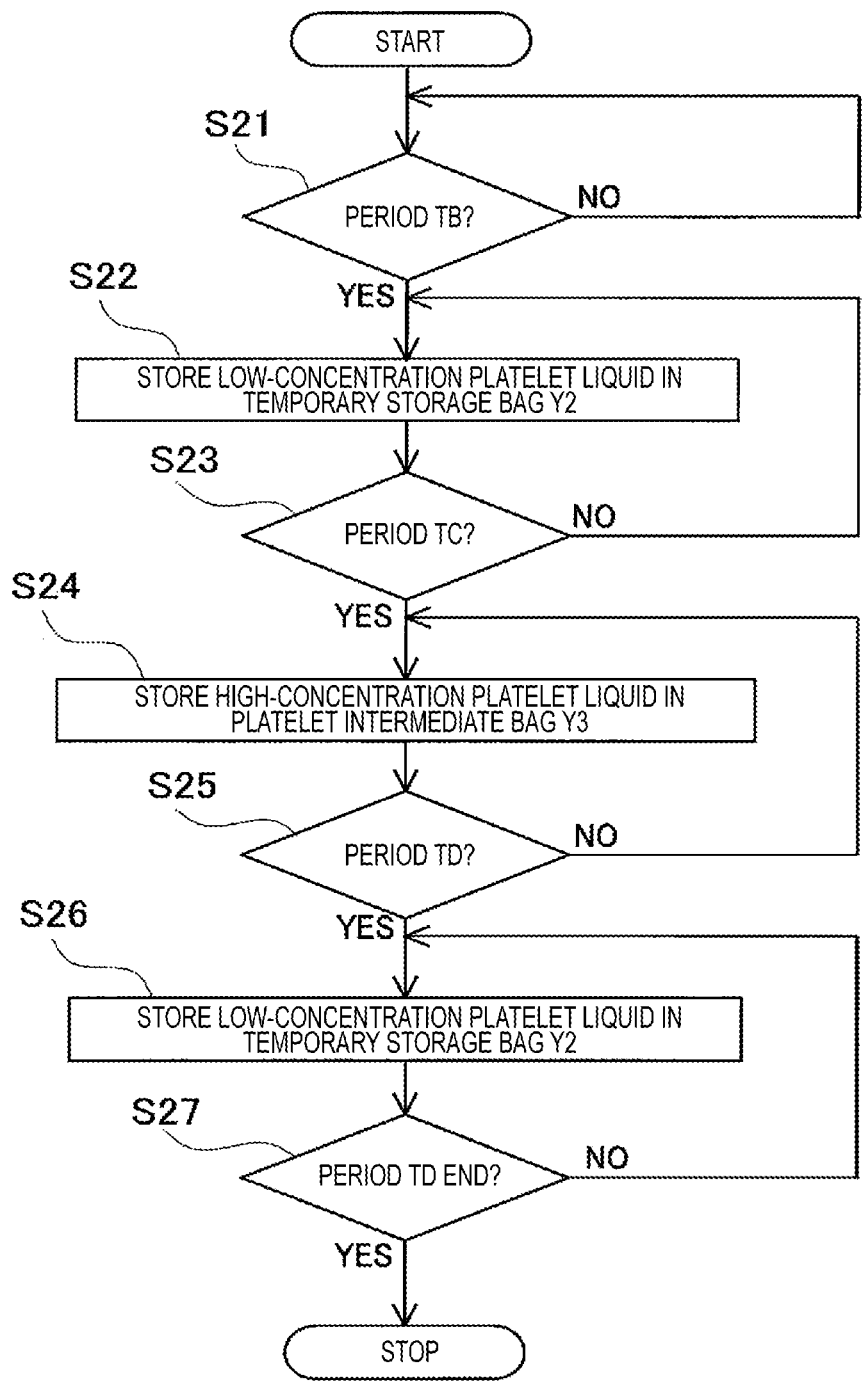
FIG. 5 is a flowchart showing an operation of a platelet liquid collecting step.

The details of step S9, and step S12 are shown as a flowchart showing the operation of the blood component separation device in FIG. 5.

The outflow period TA of platelet can be divided into three periods: a low-concentration period TB where low-concentration platelet liquid PC flows out, a high-concentration period TC where high-concentration platelet liquid PC flows out, and a low-concentration period TD where low-concentration platelet liquid PC flows out again. For obtaining high-concentration platelet liquid PC, low-concentration platelet liquid PC is not required.

In the present embodiment, as shown in FIG. 10, after the turbidity sensor C2 detects platelet PLT in the acceleration step, or in other words, when it is determined as the low-concentration period TB (S21: YES), the second on-off valve V2 is closed, the fifth on-off valve V5 is opened, and platelet liquid PC of the low-concentration period TB in FIG. 20 is stored in the temporary storage bag Y2 (S22). At this time, since the temporary storage bag Y2 also stores the whole blood flowing therein, low-concentration platelet liquid PC is stored in the temporary storage bag Y2 in the condition that it is mixed with the whole blood. Also at this time, the first blood pump P1 is kept driven, and the whole blood sampled from the blood donor is kept stored in the temporary storage bag Y2.

The temporary storage bag Y2 is used not only as a whole blood bag but also as a buffy coat bag.

Figure 11:
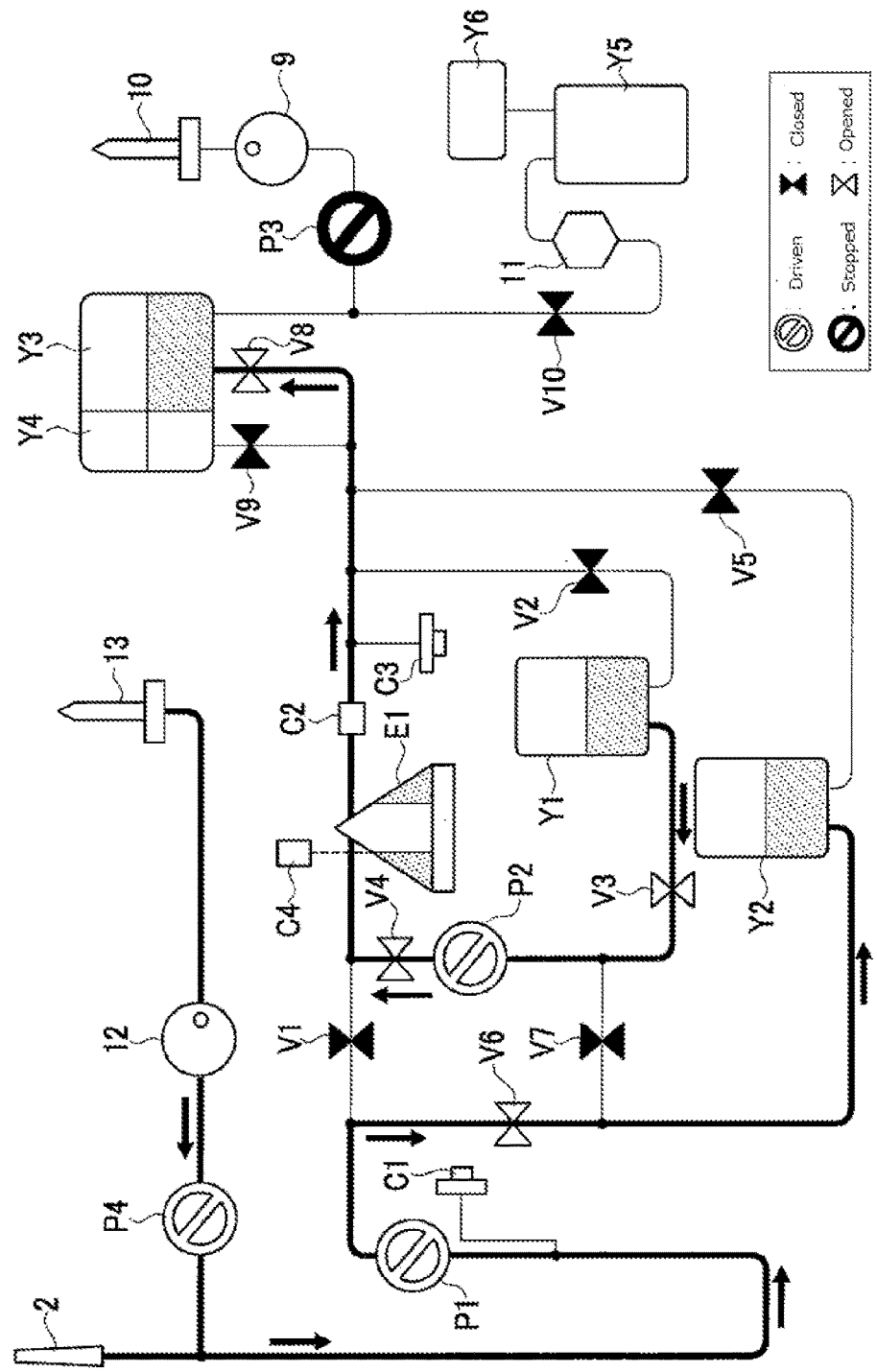
FIG. 11 is a diagram showing a step of storing a high-concentration platelet liquid in the fifth step (circulation and acceleration step).

Then when the turbidity sensor C2 detects that platelet liquid PC has high concentration, it is determined as the high-concentration period TC (S23: YES), and as shown in FIG. 11, the fifth on-off valve V5 is closed, and the eighth on-off valve V8 is opened. This makes it possible to store high-concentration platelet liquid PC flowing out during the high-concentration period TC in the platelet intermediate bag Y3 (S24).

If the current cycle is not the last cycle (S7: NO), also in this case, the first blood pump P1 is kept driven, and the whole blood sampled from the blood donor is kept stored in the temporary storage bag Y2 via the sixth on-off valve V6.

Figure 12:
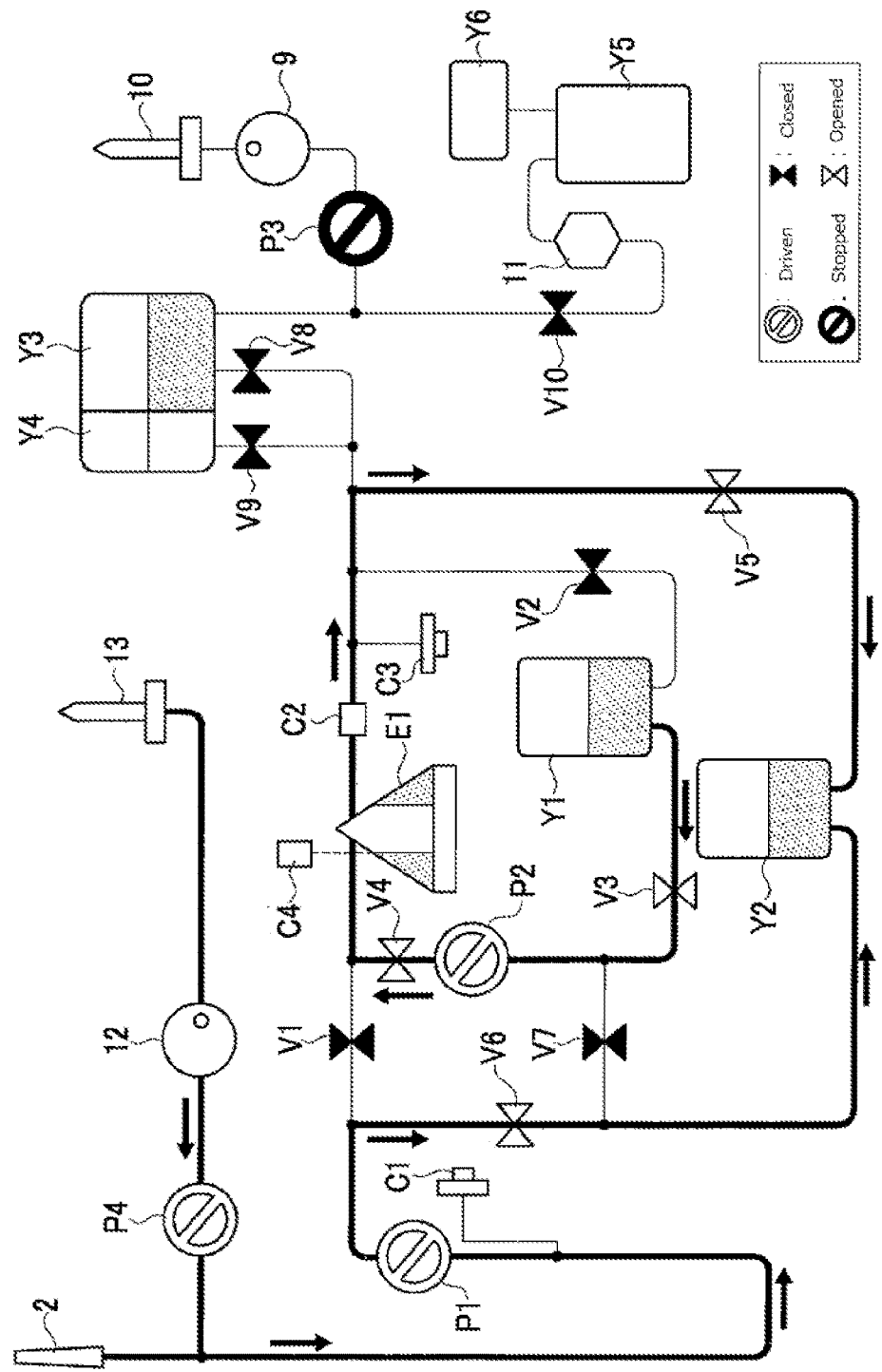
FIG. 12 is a diagram showing a step of recovering a low-concentration platelet liquid in the fifth step (circulation and acceleration step).
Figure 13:
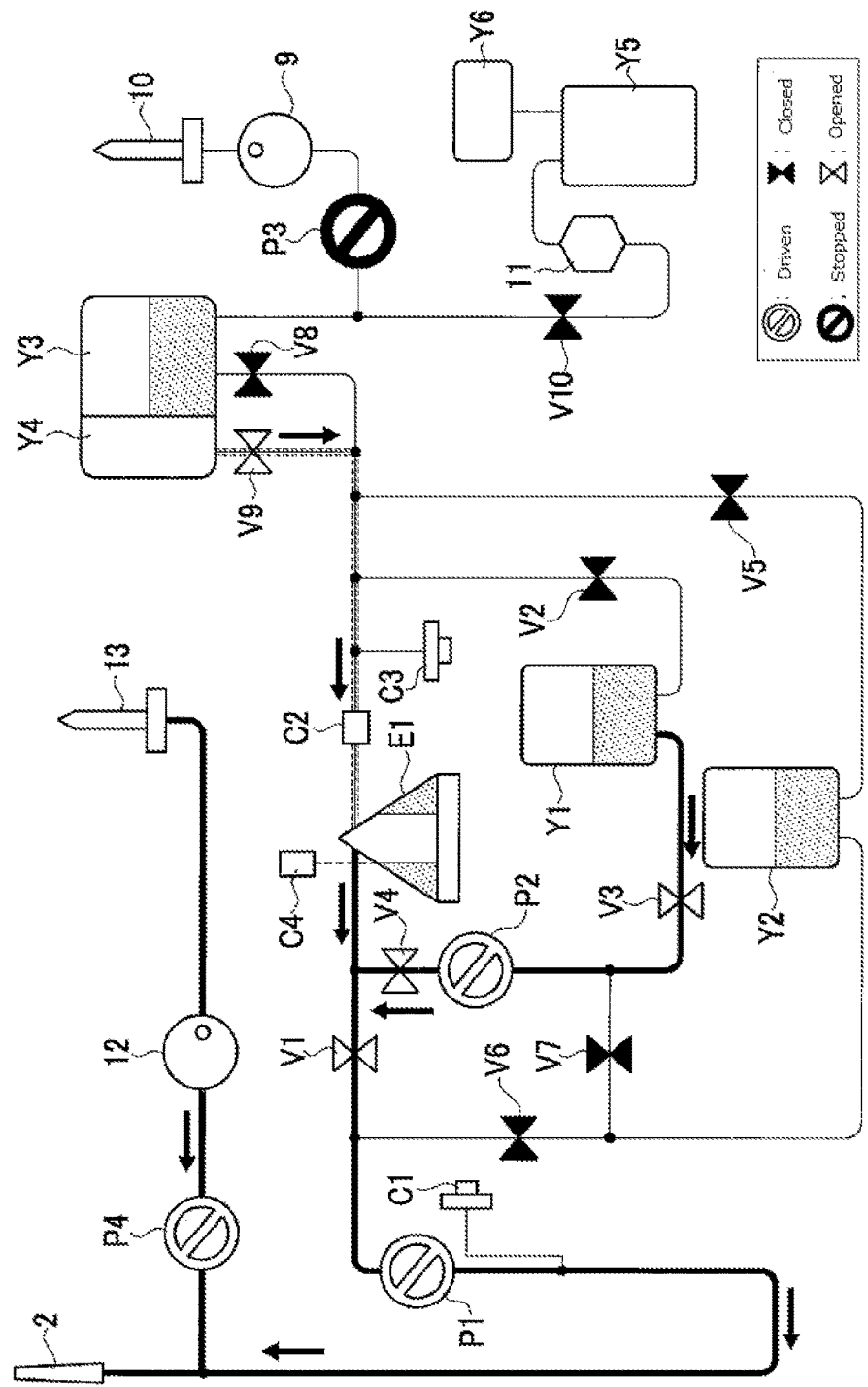
FIG. 13 is a diagram showing a blood returning step.

Then when a predetermined amount of high-concentration platelet liquid PC has been stored in platelet intermediate bag Y3, it is determined as the low-concentration period TD (S25: YES), and as shown in FIG. 12, the eighth on-off valve V8 is closed so as not to allow low-concentration platelet liquid PC to flow into the platelet intermediate bag Y3, and the fifth on-off valve V5 is opened. This makes it possible to store low-concentration platelet liquid PC flowing out during the low-concentration period TD in the temporary storage bag Y2 again (S26).

If the current cycle is not the last cycle (S7:NO), also in this case, the first blood pump P1 is kept driven, and the whole blood sampled from the blood donor is kept stored in the temporary storage bag Y2 via the sixth on-off valve V6.

The amount of high-concentration platelet liquid PC stored in the platelet intermediate bag Y3 can be easily adjusted by controlling the open time of the eighth on-off valve V8 on the basis of the flow rate of platelet liquid PC flowing out of the centrifugal bowl E1.

Then when collection of the predetermined amount of platelet liquid PC ends, or in other words, when a predetermined time has lapsed from opening of the eighth on-off valve V8, it is determined that the low-concentration period TD ends (S27: YES), and it is determined that flowing out of platelet liquid PC ends, and the process proceeds to the blood returning step shown in FIG. 13 (S10, S13).

To be more specific, blood returning for returning the blood remaining in the centrifugal bowl E1 to the blood donor is started by stopping rotation of the centrifugal bowl E1, closing the sixth on-off valve V6, and the fifth on-off valve V5, opening the first on-off valve V1, and the ninth on-off valve V9, and reversely rotating the first blood pump P1. The speed of the reverse rotation of the first blood pump P1 is set to be double the speed of the forward rotation to reduce the time require for the blood returning. The second blood pump P2 is driven as necessary to return plasma PPP that is excessively collected and stored in the plasma bag Y1.

Figure 14:
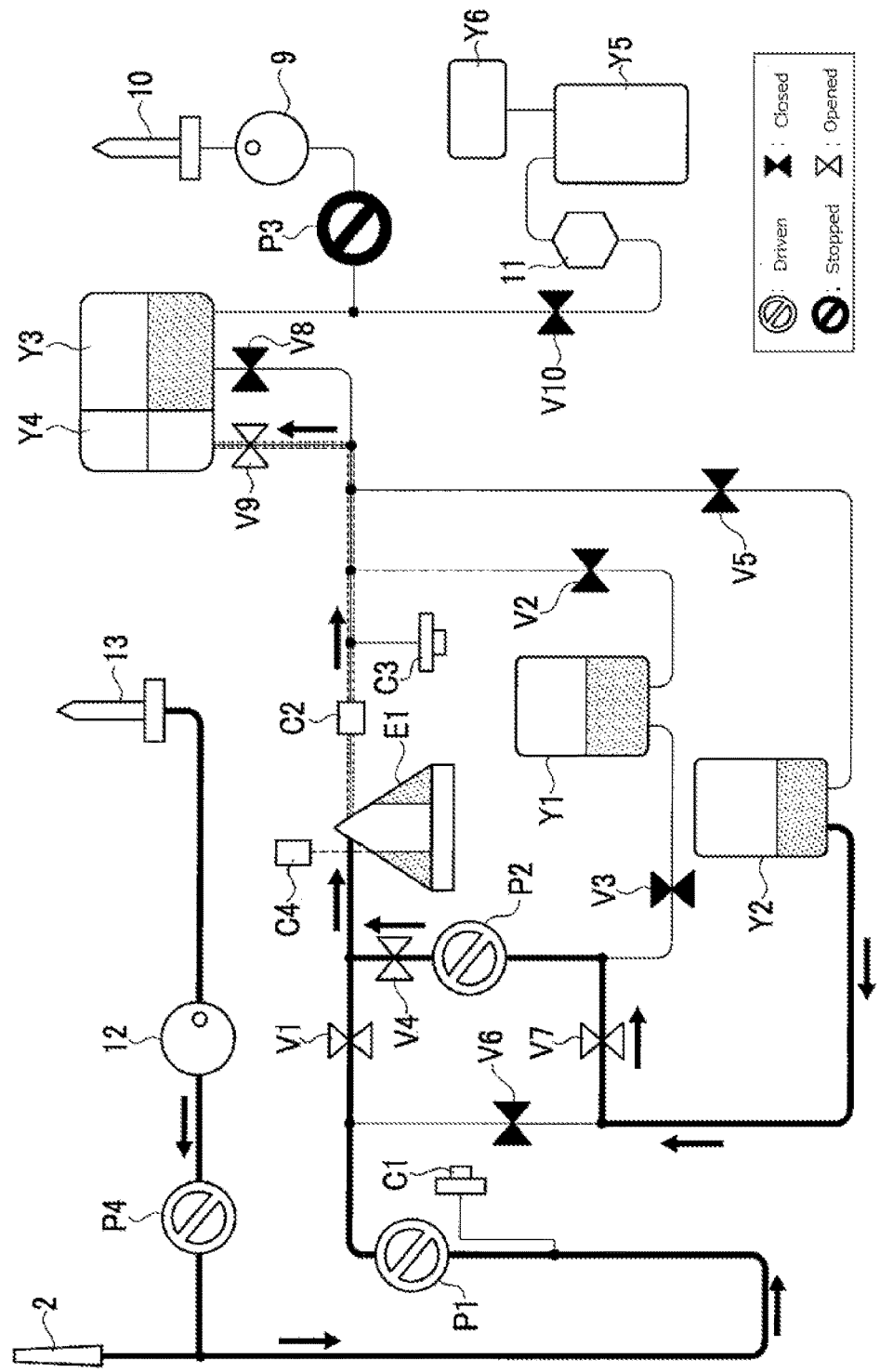
FIG. 14 is a diagram showing the first step of the second cycle.

When the blood returning ends, the whole process is terminated if the current cycle is the last cycle (S7: YES). If the current cycle is not the last cycle (S7: NO), as shown in FIG. 14, rotation of the centrifugal bowl E1 is started, and the first blood pump P1 is forwardly rotated again, and blood sampling is resumed. The air in the centrifugal bowl E1 (indicated by the dotted line) flows out from the outflow channel 19 situated in an inner circumferential part of the centrifugal bowl E1 while it is pushed by plasma PPP. The flowing out air is stored in the air bag Y4 via the open ninth on-off valve V9. At this time, also the blood stored in the temporary storage bag Y2 is allowed to flow into the centrifugal bowl E1 through the fourth on-off valve V4 simultaneously by opening the seventh on-off valve V7, and driving the second blood pump P2 (S14). At this time, the third on-off valve V3 is closed so that a fluid will not flow into the plasma bag Y1.

Figure 15:
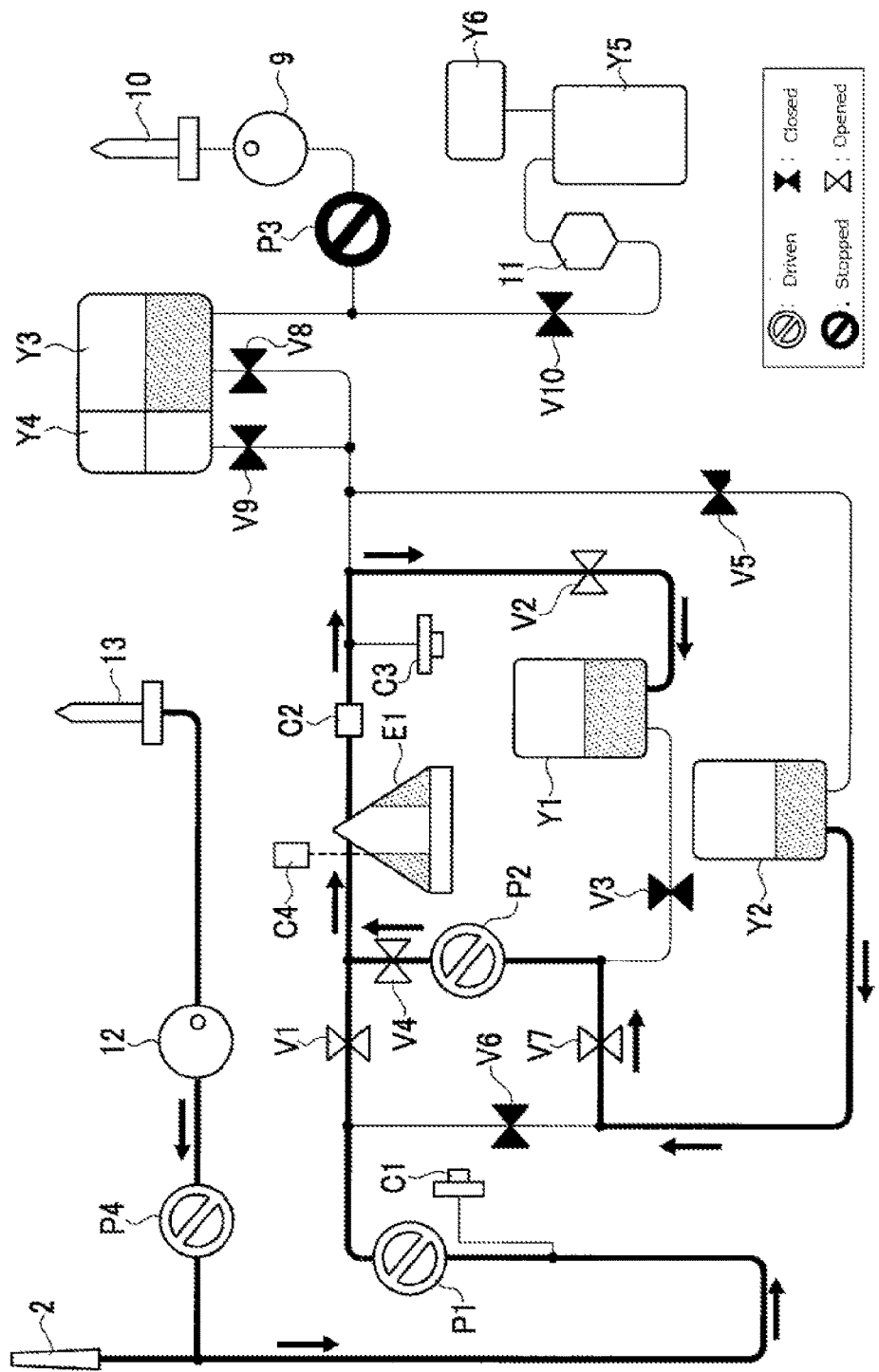
FIG. 15 is a diagram showing the second step of the second cycle.

Then when the turbidity sensor C2 detects that the fluid flowing in the tube changes from the air to plasma PPP, the ninth on-off valve V9 is closed, and the second on-off valve V2 is opened as shown in FIG. 15 to store plasma PPP overflowing from the centrifugal bowl E1 in the plasma bag Y1.

Figure 16:
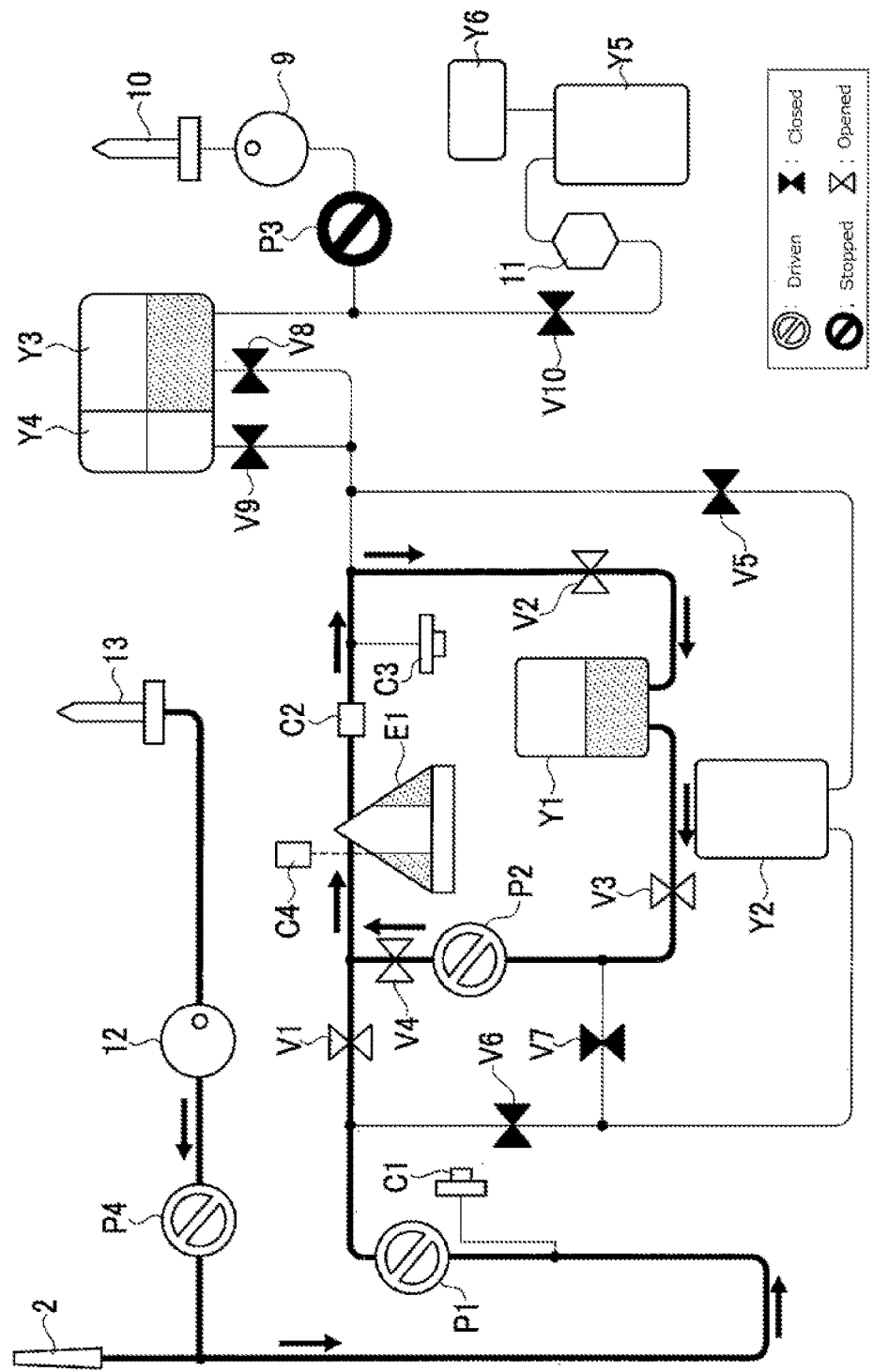
FIG. 16 is a diagram showing the third step of the second cycle.

Then when it is confirmed that that the entire blood in the temporary storage bag Y2 has returned to the centrifugal bowl E1, and it is confirmed that a predetermined amount of plasma PPP has been stored in the plasma bag Y1 (S4: YES), if the current cycle is not the last cycle (S7: NO), as shown in FIG. 16 (the same state as in FIG. 8), the second blood pump P2 is kept driven, the seventh on-off valve V7 is closed, and the third on-off valve V3 is opened so as to mix plasma PPP stored in the plasma bag Y1 with the whole blood and feed the mixture to the centrifugal bowl E1, and thus a critical flow step of plasma PPP is started. The process is followed by the step (circulation step) in FIG. 9.

This cycle is repeated normally three times or four times until a predetermined amount of platelet PLT is secured on the basis of the recommended cycle number of the platelet collecting operation calculated by the donor operation simulator 30. For example, in the case where the recommended cycle number of the platelet collecting operation is calculated to be three by the donor operation simulator 30, blood sampling is conducted in parallel during the circulation period TF2, and the acceleration period TG2 of the second cycle to store whole blood in the temporary storage bag Y2 when the operation ends with the third cycle. Then at the time of blood sampling of the third cycle, the blood in the temporary storage bag Y2 is mixed with the whole blood, and fed to the centrifugal bowl E1. And blood sampling is not conducted during the circulation period TF3, and the acceleration period TG3 in the third cycle. This is because the fourth cycle is not conducted.

When the operation ends with the third cycle, upon end of the blood returning in the third cycle, the blood sampling needle 2 is removed from the blood donor and the blood sampling ends.

Figure 17:
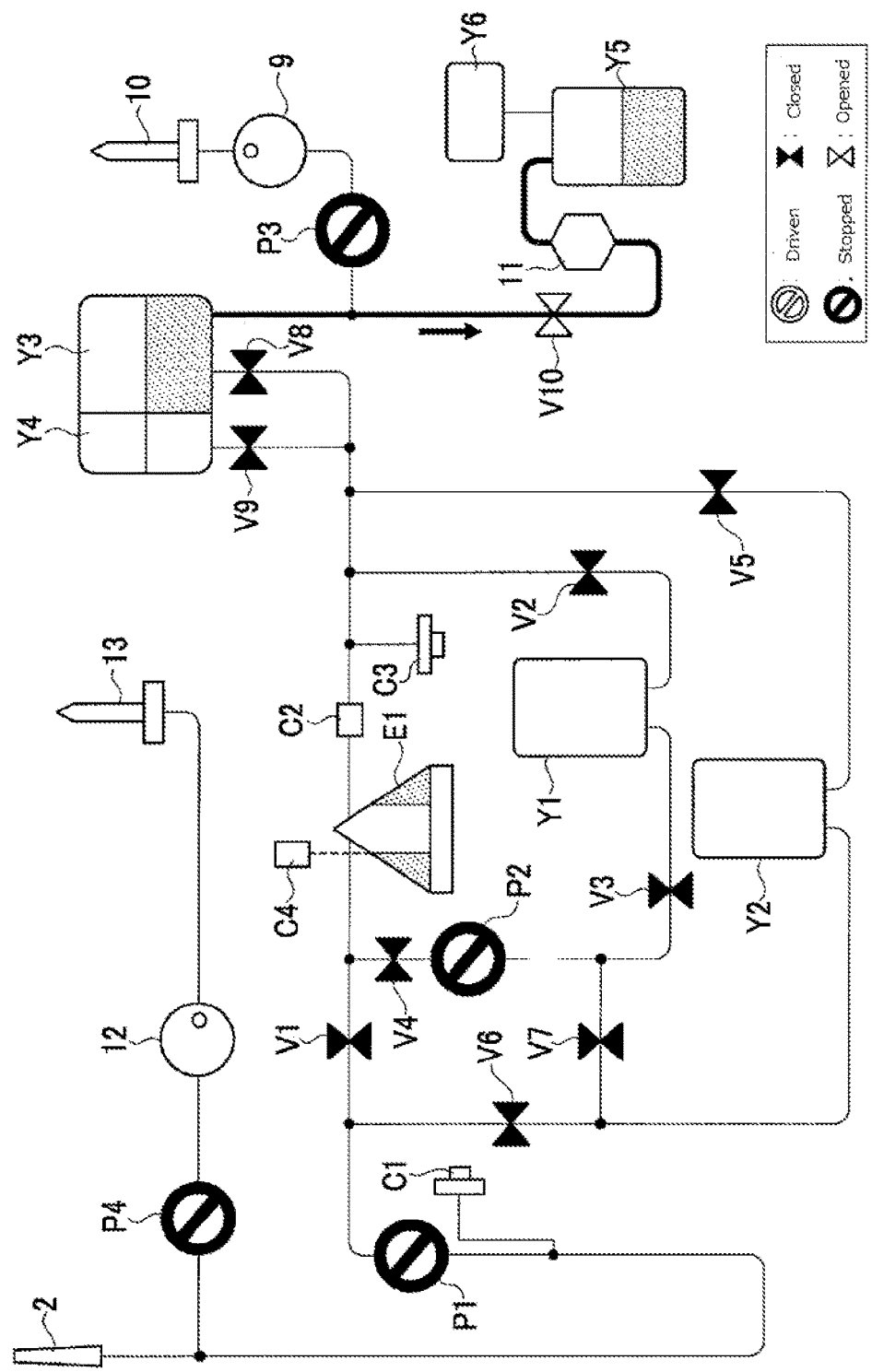
FIG. 17 is a diagram showing a step of processing a platelet liquid.

Thereafter, as shown in FIG. 17, the tenth on-off valve V10 is opened, and high-concentration platelet liquid PC and the platelet preservative liquid stored in the platelet intermediate bag Y3 are injected into the platelet bag Y5 via the white blood cell removal filter 11. At this time, the air that has exists in the platelet bag Y5 moves to the air bag Y6.

Figure 18:
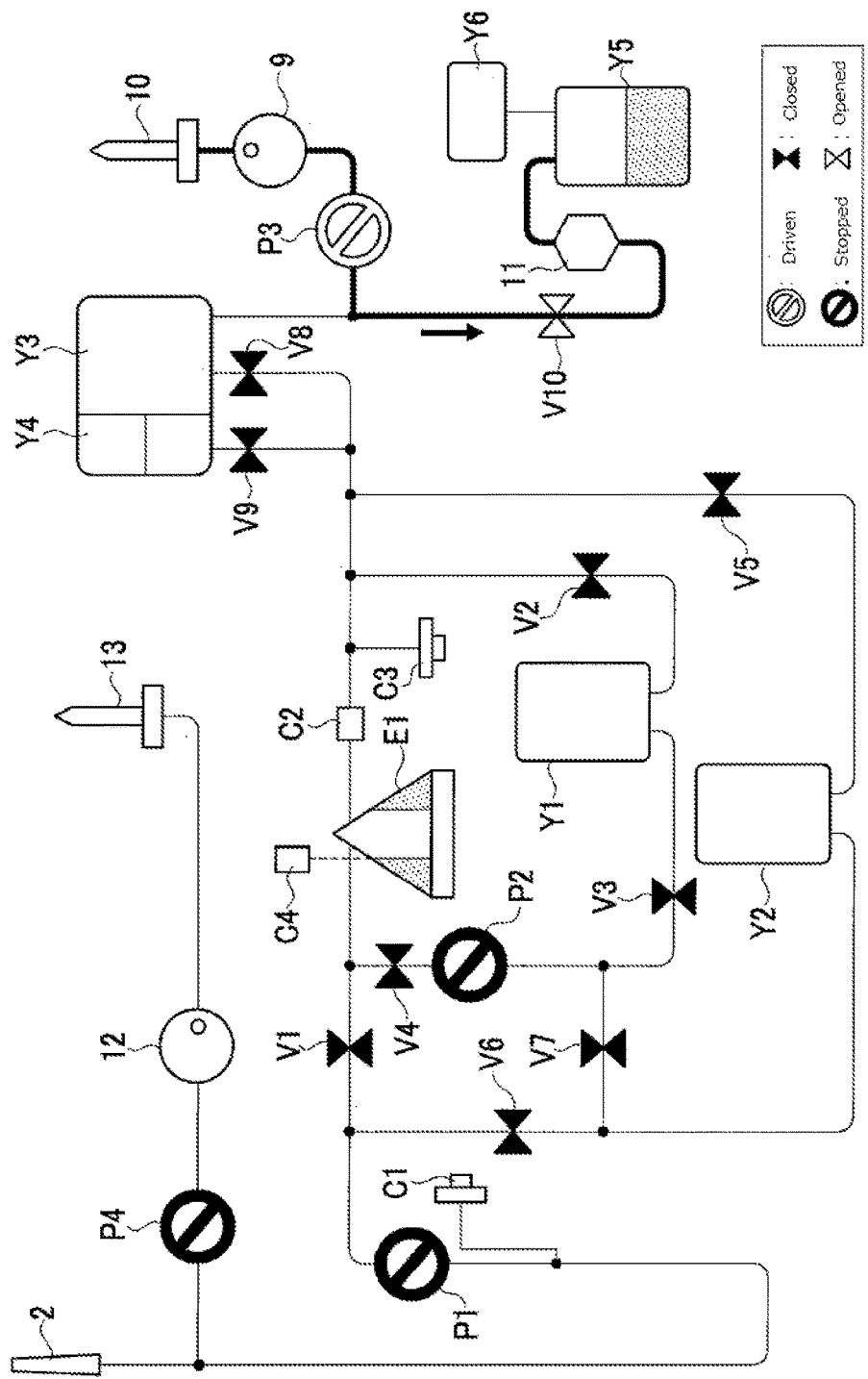
FIG. 18 is a diagram showing the final process of a platelet liquid.

After confirming that high-concentration platelet liquid PC stored in the platelet intermediate bag Y3 has wholly exited, the third blood pump P3 is driven as shown in FIG. 18, and the platelet preservative liquid remaining in the platelet preservative liquid bottle is injected into the platelet bag Y5 via the sterilization filter 9 and the white blood cell removal filter 11 by means of the needle 10 connecting to the platelet preservative liquid bottle. In this manner, high-concentration platelet liquid PC remaining in the white blood cell removal filter 11 that has been filtered is collected. Then the two tubes of the platelet bag Y5 are hermetically sealed. This completes the platelet bag Y5 in which high-concentration platelet liquid PC is stored.

Here, a method of calculating a recommended cycle number of the platelet collecting operation conducted by the donor operation simulator 30 before the start of the blood sampling will be described.

As shown in FIG. 21, a preparation platelet recovery rate (a rate of the number of platelets actually collected in the platelet bag Y5 as a preparation to the number of platelets in the blood being processed) varies depending on the sex. To be more specific, the preparation platelet recovery rate tends to be smaller for female blood donors than for male blood donors in donors having the same cycle (blood donors having the same cycle number of the platelet collecting operation).

As the cycle number of the platelet collecting operation (the processing amount of blood) increases, the difference betweenmale and female (predetermined value α) in the preparation platelet recovery rate tends to be large. For example, as shown in FIG. 21, the predetermined value α is 2% for 2-cycle donors, 4% for 3-cycle donors, and 5% for 4-cycle donors, and the predetermined value α increases with the cycle number of the platelet collecting operation.

Thus, in the present embodiment, the donor operation simulator 30 varies the value of the predicted platelet recovery rate according to the sex. That is, the donor operation simulator 30 sets the predicted platelet recovery rate calculated from any blood count value (hematocrit value and platelet concentration of the preliminarily sampled blood) to be smaller by a predetermined value α when the blood donor is female than when the blood donor is male. For example, the donor operation simulator 30 calculates the predicted platelet recovery rate to any blood count value as X % for a blood donor, and calculates as (x−α)% for a female blood donor. X and α each represent any number of 0 or more.

The donor operation simulator 30 calculates a recommended cycle number of the platelet collecting operation on the basis of the predicted platelet recovery rate calculated according to the sex. Thus, between a male and a female having the same blood count value, the recommended cycle number or the recommended processing amount of the platelet collecting operation can vary.

Hereinafter, description will be made byway of specific cases. For example, regarding the blood count value of the blood donor, the HCT value (hematocrit value) is assumed to be 42%, and the PLT value (platelet concentration) is assumed to be 23×10⁴/μL. A target number of units of platelets is assumed to be 10 units ($1.95 \times 10^{11}$ to $2.94 \times 10^{11}$).

At this time, conventionally, the predicted platelet recovery rate was assumed to be, for example, 78% regardless of the sex, and on the basis of the predicted platelet recovery rate, the recommended cycle number of the platelet collecting operation, and the predicted PLT number (predicted number of collected platelets) were calculated. According to this, the recommended cycle number of the platelet collecting operation was determined to be three regardless of whether the blood donor was male or female as shown in FIG. 22, and the predicted PLT number was calculated as $2.04 \times 10^{11}$ (in the drawing, indicated as "2.04×10e11") which is approximate to the lower limit value of the target number of units (10 units).

However, as shown in FIG. 22, when the process was actually conducted by taking the cycle number of the platelet collecting operation as three, the expected preparation PLT number (the number of platelets that are actually collected in the platelet bag Y5) was $2.04 \times 10^{11}$ when the blood donor was male, but $1.93 \times 10^{11}$ (in the drawing, indicated as "1.93×10e11") when the blood donor was female. That is, although the blood was processed according to the recommended cycle number of the platelet collecting operation, 10 units of platelets could be collected when the blood donor was male, but 10 units of platelets could not be collected when the blood donor was female.

As described above, in such a particular case where the predicted PLT number is approximate to the lower limit value of the target number of units, inadequacy of units can occur when the blood donor is female due to the influence of difference in the circulating blood volume or the difference in the blood flow condition between male and female.

In contrast to this, in the present embodiment, as described in the example of the blood count value, the donor operation simulator 30 calculates the predicted platelet recovery rate to be, for example, 78% when the blood donor is male, and calculates the predicted platelet recovery rate to be, for example, 74% when the blood donor is female. Then the donor operation simulator 30 calculates a recommended cycle number and a predicted PLT number of the platelet collecting operation on the basis of the predicted platelet recovery rate.

Thus, as shown in FIG. 23, the donor operation simulator 30 calculates the recommended cycle number to be three when the blood donor is male, and calculates the predicted PLT number to be $2.04 \times 10^{11}$. On the other hand, the donor operation simulator 30 calculates the recommended cycle number to be four, and calculates the predicted PLT number to be $2.50 \times 10^{11}$ when the blood donor is female, because if the recommended cycle number is calculated to be three, the predicted PLT number is $1.93 \times 10^{11}$, and inadequacy of units would occur.

As shown in FIG. 23, the process was actually conducted while setting the cycle number of the platelet collecting operation to be four for a female blood donor, and the expected preparation PLT number was $2.50 \times 10^{11}$. In other words, 10 units of platelets could be collected also for a female blood donor.

As described above, the process is not influenced by the difference in circulating blood volume or the difference in blood flow condition between male and female, and inadequacy of units does not occur regardless of whether the blood donor is male or female.

The range of the predetermined value a can be set, for example, as in FIG. 24. In the example shown in FIG. 24, the range of the predetermined value α is set for 1-cycle donor to 5-cycle donor. As the cycle number increases and thus the processing amount of blood increases, the upper limit value of the predetermined value a increases. In FIG. 24, for example, "3-cycle donor" refers to the case where the recommended cycle number of the platelet collecting operation is calculated to be three assuming that the blood donor is male. In this case, when the blood donor is female, the value obtained by subtracting 0 to 6.0% from the predicted platelet recovery rate when the blood donor is male is set as a predicted platelet recovery rate.

These are the description for a method of calculating a recommended cycle number by the donor operation simulator 30.

As specifically described in the above, the blood component separation device of the present embodiment has the donor operation simulator 30 that calculates a predicted platelet recovery rate from a hematocrit value and a platelet concentration of blood sampled from a blood donor, and calculates a recommended cycle number (recommended processing amount of blood) recommended for collecting a target number of units of platelets on the basis of the calculated predicted platelet recovery rate. The donor operation simulator 30 calculates the predicted platelet recovery rate calculated from any hematocrit value and any platelet concentration to be smaller by a predetermined value a when the blood donor is female than when the blood donor is male.

Therefore, it is possible to calculate the predicted platelet recovery rate accurately according to the sex of the blood donor. Therefore, it is possible to securely collect a target number of units of platelets regardless of the sex of the blood donor.

In the present embodiment, as the predicted platelet recovery rate decreases, and thus the recommended cycle number increases, the predetermined value α increases. Therefore, it is possible to securely collect a target number of units of platelets regardless of the cycle number and the sex of the blood donor.

The blood component separation device of the present embodiment conducts: a) a centrifugal separation step of introducing the blood into a centrifuge, and separating the blood into a plurality of blood components; b) a circulation flow step of introducing plasma among the separated blood components into the centrifuge together with the blood; c) a circulation and acceleration step of introducing only plasma into the centrifuge while stopping feeding of the blood into the centrifuge after the circulation flow step, allowing plasma to further circulate for a predetermined time, and then accelerating a circulation velocity, to separate and collect platelets by the centrifuge, and d) a blood returning step of returning blood components that have not been collected to the blood donor after the circulation and acceleration step, and the steps a) to d) are conducted as one cycle.

Therefore, it is possible to accurately separate platelets from other blood components. Also since the collection timing of high-concentration platelets is optimized, a larger quantity of platelets can be collected efficiently.

Second Embodiment

The approach of varying the value of the predicted platelet recovery rate according to the sex as described above can also be applied to a belt-type continuous centrifuge 50 which is other embodiment of the blood component separation device.

Figure 25:
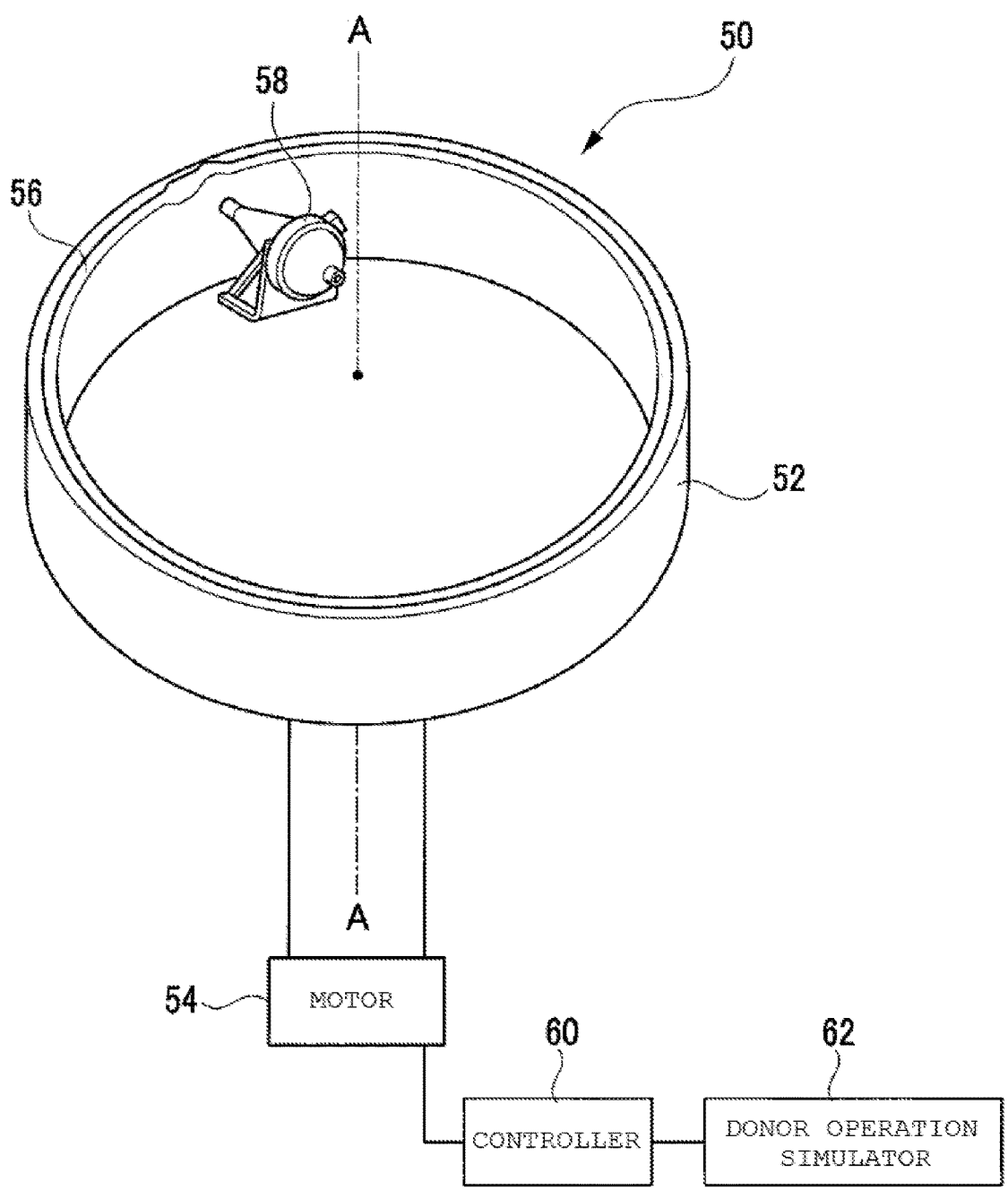
FIG. 25 is a partial perspective view of a continuous centrifuge.

As shown in FIG. 25, the continuous centrifuge 50 has a circular rotor 52, a motor 54 connected with the rotor 52, a circular (circular belt-like) separation vessel 56 disposed integrally with the rotor 52 inside the rotor 52, a fluid chamber 58 attached to the rotor 52 inside the rotor 52, a controller 60, a donor operation simulator 62 and so on.

Figure 26:
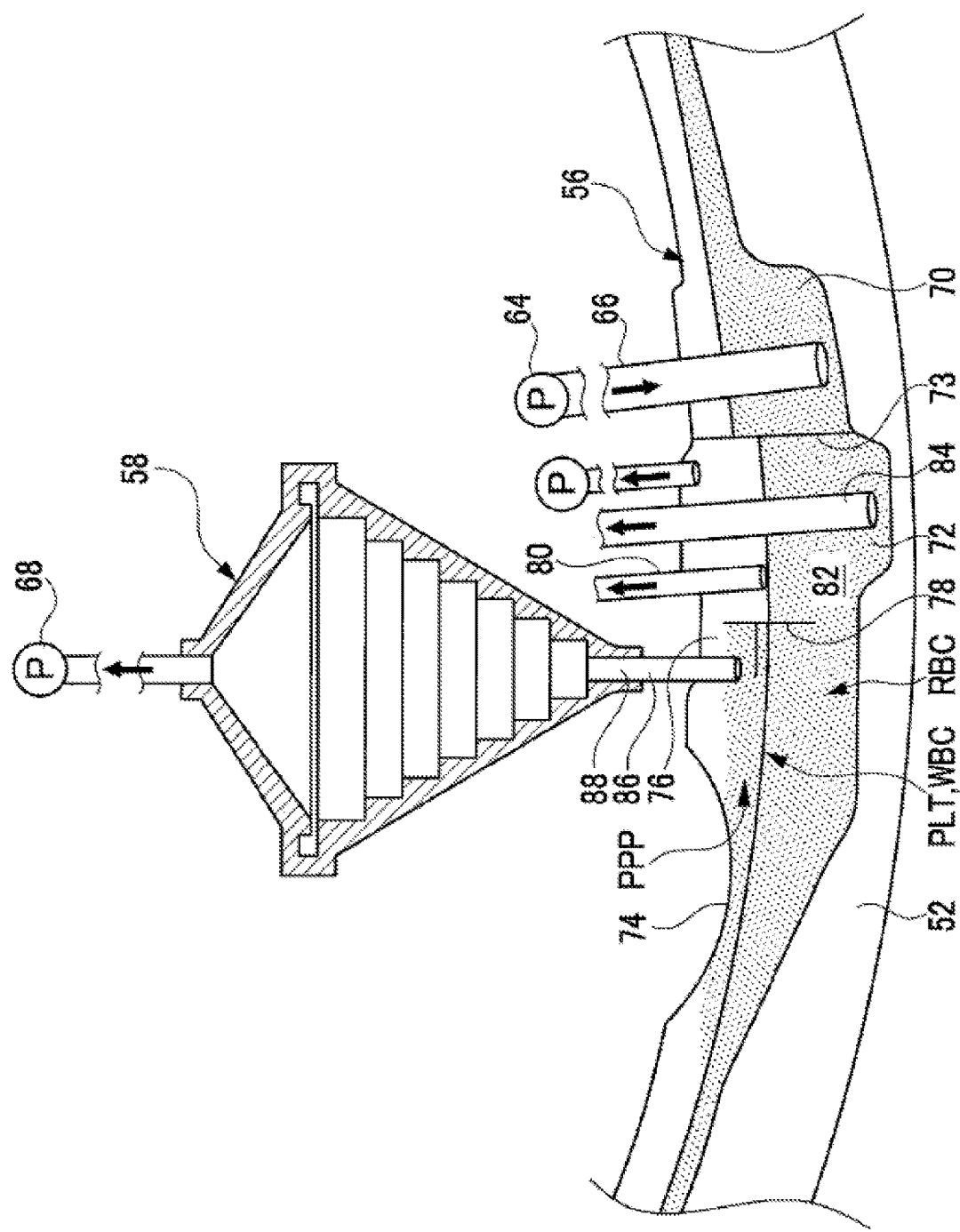
FIG. 26 is a section view of a part of a separation vessel and the vicinity of a fluid chamber.

In the continuous centrifuge 50 having such a configuration, first, the separation vessel 56 and the fluid chamber 58 are filled with blood sampled from a blood donor. To be more specific, as shown in FIG. 26, blood is flown into the separation vessel 56 from an inflow pump 64 through an inflow tube 66. Upon actuation of a collection pump 68, the blood flows from an inlet part 70 toward an outlet part 72 counterclockwise (left-hand rotating direction) in the separation vessel 56 shown in FIG. 26. The inlet part 70 and the outlet part 72 are blocked each other by a wall 73.

Further, by rotating the rotor 52 by actuating the motor 54, the separation vessel 56 and the fluid chamber 58 are rotated about the rotation axis A-A (see FIG. 1). Thus, as shown in FIG. 26, components of the blood captured at a position on the upstream side a trap dam 74 is separated by the centrifugal force. As a result, individual components of the blood are layered in descending order of the density, namely in the order of red blood cell, white blood cell, platelet, and plasma. That is, as shown in FIG. 26, the layer of red blood cell RBC is formed along the outer wall of the separation vessel 56, and the layer of plasma PPP is formed along the inner wall of the separation vessel 56. Between the layer of red blood cell RBC and the layer of plasma PPP, the layers of platelet PLT and white blood cell WBC are formed.

In the outlet part 72, plasma PPP flows to a position on the downstream side (right side in FIG. 26) of a barrier 78 through a first channel 76, and is removed through a collection line 80. Red blood cell RBC flows to a position on the downstream side of the barrier 78 through a second channel 82, and is removed through a collection line 84.

Meanwhile, in the outlet part 72, platelet PLT and white blood cell WBC remain at a position on the upstream side of the barrier 78 (left side in FIG. 26). And the remaining platelet PLT together with white blood cell WBC flow into the fluid chamber 58 through a collection line 86.

Then platelet PLT and white blood cell WBC deposit in the fluid chamber 58. At this time, due to the difference in the rate of sedimentation between platelet PLT and white blood cell WBC, platelet PLT deposits at a position farther from an inlet 88 of the fluid chamber 58 compared with white blood cell WBC. In this manner, a deposit layer of platelet PLT is formed in the fluid chamber 58. White blood cell WBC deposits between the inlet 88 and the deposit layer of platelet PLT in the fluid chamber 58.

Platelet PLT deposited in this manner is recovered from the fluid chamber 58, and collected and stored in a predetermined vessel. In this manner, platelet PLT is collected from the blood in the continuous centrifuge 50.

Here, in the present embodiment, also in the continuous centrifuge 50 as described above, the donor operation simulator 62 sets the predicted platelet recovery rate calculated from any blood count value to be smaller by a predetermined value cc when the blood donor is female than when the blood donor is male in the same manner as described above. The donor operation simulator 62 calculates a recommended processing amount of blood (a processing amount of blood recommended to collect a target number of units of platelets) on the basis of the predicted platelet recovery rate according to the sex calculated in the manner as described above.

Therefore, between male and female having the same blood count value, the recommended processing amount of blood varies. Specifically, the donor operation simulator 62 sets the recommended processing amount of blood to be larger when the blood donor is female than when the blood donor is male in the male and the female blood donors having the same blood count value. For example, in the case where the recommended processing amount of blood is set to be 1500 mL when the blood donor is male, the recommended processing amount of blood when the blood donor is female set to be 1580 mL.

Therefore, the process is not influenced by the difference in circulating blood volume or the difference in blood flow condition between male and female, and inadequacy of units does not occur regardless of whether the blood donor is male or female. Likewise in the first embodiment, as the predicted platelet recovery rate decreases, and thus the recommended processing amount of blood increases, the predetermined value α increases.

As specifically described in the above, the blood component separation device of the present embodiment has the donor operation simulator 62 that calculates a predicted platelet recovery rate from a hematocrit value and a platelet concentration of blood sampled from a blood donor, and calculates a recommended processing amount of blood recommended for collecting a target number of units of platelets on the basis of the calculated predicted platelet recovery rate. The donor operation simulator 62 calculates the predicted platelet recovery rate calculated from any hematocrit value and any platelet concentration to be smaller by a predetermined value cc when the blood donor is female than when the blood donor is male.

Therefore, it is possible to calculate the predicted platelet recovery rate accurately according to the sex of the blood donor. Therefore, it is possible to securely collect a target number of units of platelets regardless of the sex of the blood donor.

In the present embodiment, as the predicted platelet recovery rate decreases, and thus the recommended processing amount of blood increases, the predetermined value α increases. Therefore, it is possible to securely collect a target number of units of platelets regardless of the cycle number and the sex of the blood donor.

In the blood component separation device of the present embodiment, by rotating the separation vessel 56 about the rotation axis A-A while feeding blood into the circular separation vessel 56, the blood in the separation vessel 56 is separated into a plurality of blood components, and platelets are collected from the plurality of separated blood components. Thus, it is possible to accurately separate platelets from other blood components with a simple device configuration.

It goes without saying that the above embodiments are merely illustrative, and do not limit in any way, and various modification and variation without departing from the scope of the invention can be made. In the above embodiments, the temporary storage bag Y2 functions as both a buffy coat bag and a whole blood bag, a buffy coat bag and a whole blood bag may be provided in parallel as separate bags.

REFERENCE SIGNS LIST

1 Blood component separation circuit
15 Controller
E1 Centrifugal bowl
Y1 Plasma bag (first vessel)
Y2 Temporary storage bag (second vessel)
Y3 Platelet intermediate bag (third vessel)
Y4 Air bag
Y5 Platelet bag
Y6 Air bag
C2 Turbidity sensor
C4 Interface sensor
P1 First blood pump
P2 Second blood pump
P3 Third blood pump
V1 First on-off valve
V2 Second on-off valve
V3 Third on-off valve
V4 Fourth on-off valve
V5 Fifth on-off valve
V6 Sixth on-off valve
V7 Seventh on-off valve
V8 Eighth on-off valve
V9 Ninth on-off valve
V10 Tenth on-off valve
T1 to 21 Tube
PLT Platelet
PC Platelet liquid
PPP Plasma
RBC Red blood cell
WBC White blood cell
Donor operation simulator
Continuous centrifuge
52 Rotor
54 Motor
56 Separation vessel
58 Fluid chamber
62 Donor operation simulator

The invention claimed is:

1. A device for a blood component separation device, comprising:
a microcomputer that:
receives a predicted platelet recovery rate calculated from a hematocrit value of blood from a blood donor and a platelet concentration of the blood, wherein the calculated predicted platelet recovery rate is set to be smaller by a predetermined value when the blood donor is female than when the blood donor is male;
receives a recommended processing amount of the blood for collecting a target number of units of platelets, the recommended processing amount being calculated based on the calculated predicted platelet recovery rate; and
controls the blood component separation device to process the blood in accordance with the recommended processing amount.

2. The device according to claim 1, wherein the predetermined value increases as the recommended processing amount of the blood increases.

3. The device according to claim 2, wherein the microcomputer controls the blood component separation device to perform:
a) a centrifugal separation step of introducing the blood into a centrifuge, and separating the blood into a plurality of blood components;
b) a circulation flow step of introducing plasma from the plurality of blood components into the centrifuge together with the blood;
c) a circulation and acceleration step of introducing only the plasma into the centrifuge while stopping feeding of the blood into the centrifuge after the circulation flow step, allowing the plasma to further circulate for a predetermined time, and then accelerating a circulation velocity, to separate and collect platelets in the centrifuge; and
d) a blood returning step of returning blood components that have not been collected to the blood donor after the circulation and acceleration step are conducted,
wherein steps a) to d) correspond to one blood processing cycle, and
wherein the recommended processing amount corresponds to a recommended number of blood processing cycles.

4. The device according to claim 3, wherein the microcomputer controls the blood component separation device to perform the recommended number of blood processing cycles.

5. The device according to claim 1, wherein
the microcomputer controls a separation vessel to rotate about an axial center while feeding the blood into the separation vessel so that the blood in the separation vessel is into a plurality of blood components, and platelets are collected from the plurality of separated blood components.

6. The device according to claim 1, wherein the microcomputer controls the blood component separation device to perform:

a) a centrifugal separation step of introducing the blood into a centrifuge, and separating the blood into a plurality of blood components;
b) a circulation flow step of introducing plasma from the plurality of blood components into the centrifuge together with the blood;
c) a circulation and acceleration step of introducing only the plasma into the centrifuge while stopping feeding of the blood into the centrifuge after the circulation flow step, allowing the plasma to further circulate for a predetermined time, and then accelerating a circulation velocity, to separate and collect platelets in the centrifuge; and
d) a blood returning step of returning blood components that have not been collected to the blood donor after the circulation and acceleration step are conducted,
wherein steps a) to d) correspond to one blood processing cycle, and
wherein the recommended processing amount corresponds to a recommended number of blood processing cycles.

7. The device according to claim 6, wherein the microcomputer controls the blood component separation device to perform the recommended number of blood processing cycles.

8. The device according to claim 1,
wherein the predetermined value increases as the recommended processing amount of the blood increases; and
wherein the microcomputer controls a separation vessel to rotate about an axial center while feeding the blood into the separation vessel so that the blood in the separation vessel is separated into a plurality of blood components, and platelets are collected from the plurality of blood components.

9. A method for a blood component separation device, comprising:
calculating a predicted platelet recovery rate from a hematocrit value of blood from a blood donor and a platelet concentration of the blood, wherein the calculated predicted platelet recovery rate is set to be smaller by a predetermined value when the blood donor is female than when the blood donor is male; and
calculating a recommended processing amount of the blood recommended for collecting a target number of units of platelets based on the calculated predicted platelet recovery rate.

10. The method according to claim 9, further comprising:
a) a centrifugal separation step of introducing the blood into a centrifuge, and separating the blood into a plurality of blood components;
b) a circulation flow step of introducing plasma from the plurality of blood components into the centrifuge together with the blood;
c) a circulation and acceleration step of introducing only the plasma into the centrifuge while stopping feeding of the blood into the centrifuge after the circulation flow step, allowing the plasma to further circulate for a predetermined time, and then accelerating a circulation velocity, to separate and collect platelets in the centrifuge; and
d) a blood returning step of returning blood components that have not been collected to the blood donor after the circulation and acceleration step are conducted,
wherein steps a) to d) correspond to one blood processing cycle.

11. The method according to claim 10, wherein the recommended processing amount corresponds to a recommended number of blood processing cycles.

12. The method according to claim 11, further comprising:
controlling the blood component separation device to perform the recommended number of blood processing cycles.

13. The method according to claim 9, further comprising:
controlling the blood component separation device to process the blood in accordance with the recommended processing amount.

\* \* \* \* \*